(12) United States Patent
Nathwani et al.

(10) Patent No.: US 11,723,925 B2
(45) Date of Patent: *Aug. 15, 2023

(54) ROR1 CAR T-CELLS

(71) Applicant: UCL Business LTD, London (GB)

(72) Inventors: Amit Nathwani, London (GB); Satyen Gohil, London (GB); Marco Della Peruta, London (GB)

(73) Assignee: UCL Business LTD, London (GB)

( * ) Notice: Subject to any disclaimer, the term of this patent is extended or adjusted under 35 U.S.C. 154(b) by 685 days.

This patent is subject to a terminal disclaimer.

(21) Appl. No.: 16/628,450

(22) PCT Filed: Jul. 5, 2018

(86) PCT No.: PCT/GB2018/051915
§ 371 (c)(1),
(2) Date: Jan. 3, 2020

(87) PCT Pub. No.: WO2019/008378
PCT Pub. Date: Jan. 10, 2019

(65) Prior Publication Data
US 2020/0405759 A1 Dec. 31, 2020

(30) Foreign Application Priority Data
Jul. 5, 2017 (GB) ..................... 1710836

(51) Int. Cl.
*A61K 35/17* (2015.01)
*A61P 35/02* (2006.01)
*C07K 14/725* (2006.01)
*C07K 14/705* (2006.01)
*C07K 16/28* (2006.01)

(52) U.S. Cl.
CPC ............. *A61K 35/17* (2013.01); *A61P 35/02* (2018.01); *C07K 14/7051* (2013.01); *C07K 14/70521* (2013.01); *C07K 14/70578* (2013.01); *C07K 16/2803* (2013.01)

(58) Field of Classification Search
CPC ..... A61K 35/17; A61P 35/02; C07K 14/7051; C07K 14/70521; C07K 14/70578; C07K 16/2803

See application file for complete search history.

(56) References Cited

U.S. PATENT DOCUMENTS

| | | | |
|---|---|---|---|
| 8,076,459 B2 | 12/2011 | Hofmeister et al. | |
| 9,102,736 B2 | 8/2015 | Hofmeister et al. | |
| 11,466,083 B2* | 10/2022 | Nathwani | ........... C07K 16/2803 |
| 2008/0279858 A9* | 11/2008 | Umana | ................. A61K 38/179 |
| | | | 536/23.53 |
| 2012/0100152 A1* | 4/2012 | Roberts | ................... A61P 29/00 |
| | | | 435/69.6 |
| 2013/0273073 A1 | 10/2013 | Kipps et al. | |
| 2013/0281922 A1 | 10/2013 | Teige | |
| 2015/0306141 A1 | 10/2015 | Jensen et al. | |
| 2016/0017058 A1* | 1/2016 | Kim | ................... C07K 16/2887 |
| | | | 530/387.3 |
| 2018/0127504 A1* | 5/2018 | Wu | ..................... C07K 16/3069 |
| 2020/0030454 A1 | 1/2020 | Lannutti et al. | |
| 2022/0193130 A1* | 6/2022 | Ogrunc | .............. C07K 14/7051 |

FOREIGN PATENT DOCUMENTS

| | | | |
|---|---|---|---|
| EP | 2789630 A1 | 10/2014 | |
| JP | 09020798 A | * | 1/1997 |
| WO | WO-2005/040220 A1 | 5/2005 | |
| WO | WO-2007/146957 A2 | 12/2007 | |
| WO | WO-2010/124188 A1 | 10/2010 | |
| WO | WO-2011/054007 A1 | 5/2011 | |
| WO | WO-2011/079902 A2 | 7/2011 | |
| WO | WO-2012/045085 A1 | 4/2012 | |
| WO | WO-2012/075158 A1 | 6/2012 | |
| WO | WO-2012/076066 A1 | 6/2012 | |
| WO | WO-2012/076727 A1 | 6/2012 | |
| WO | WO-2014/031174 A1 | 2/2014 | |
| WO | WO-2014/167022 A1 | 10/2014 | |
| WO | WO-2015/184203 A1 | 12/2015 | |
| WO | WO-2015/184207 A1 | 12/2015 | |
| WO | WO-2016/016343 A1 | 2/2016 | |
| WO | WO-2016/016344 A1 | 2/2016 | |
| WO | WO-2016/039321 A1 | 3/2016 | |
| WO | WO-2016/055592 A1 | 4/2016 | |
| WO | WO-2016/055593 A1 | 4/2016 | |
| WO | WO-2016/094873 A2 | 6/2016 | |
| WO | WO-2016/115559 A1 | 7/2016 | |
| WO | WO-2016/124553 A1 | 8/2016 | |
| WO | WO-2016/187216 A1 | 11/2016 | |
| WO | WO-2016/187220 A2 | 11/2016 | |

(Continued)

OTHER PUBLICATIONS

Gianpietro Dotti et al. Semin Oncol, October; 41(5): 661-666. doi:10.1053/j.seminoncol.2014.08.005. (Year: 2014).*
Gohil, S. et al., Pre-clinical development of novel ROR1 chimeric antigen receptor T cells and bispecific T cell engagers, 212 pages (Mar. 1, 2019).
Gohil et al., A Novel Humanised ROR1 Bi-Specific T-Cell Engager Molecule for the Treatment of Chronic Lymphocytic Leukaemia, Blood (Dec. 2, 2016), 128(22):3244, 642. CLL: Therapy, Excluding Transplantation: Poster II (<https://doi.org/10.1182/blood.V128.22.3244.3244>).
Gohil et al., A ROR1 Bispecific T Cell Engager for the Treatment of Chronic Lymphocytic Leukaemia Demonstrates Enhanced Function Following Ibrutinib Treatment, Blood (Dec. 7, 2017), 130(Supplement 1):4316, 642. CLL: Therapy, Excluding Transplantation: Poster III (<https://doi.org/10.1182/blood.V130.Suppl_1.4316.4316>).

(Continued)

*Primary Examiner* — Arthur S Leonard
*Assistant Examiner* — Masudur Rahman
(74) *Attorney, Agent, or Firm* — Choate, Hall & Stewart LLP; Brenda Herschbach Jarrell; Dana M. Dankss

(57) ABSTRACT

There is described a chimeric antigen receptor (CAR) which comprises an antigen binding domain which selectively binds to Receptor Tyrosine Kinase Like Orphan Receptor 1 (ROR1), and its use. Also described is a T cell comprising the CAR and its use in the treatment of cancer.

16 Claims, 12 Drawing Sheets

Figure 1:
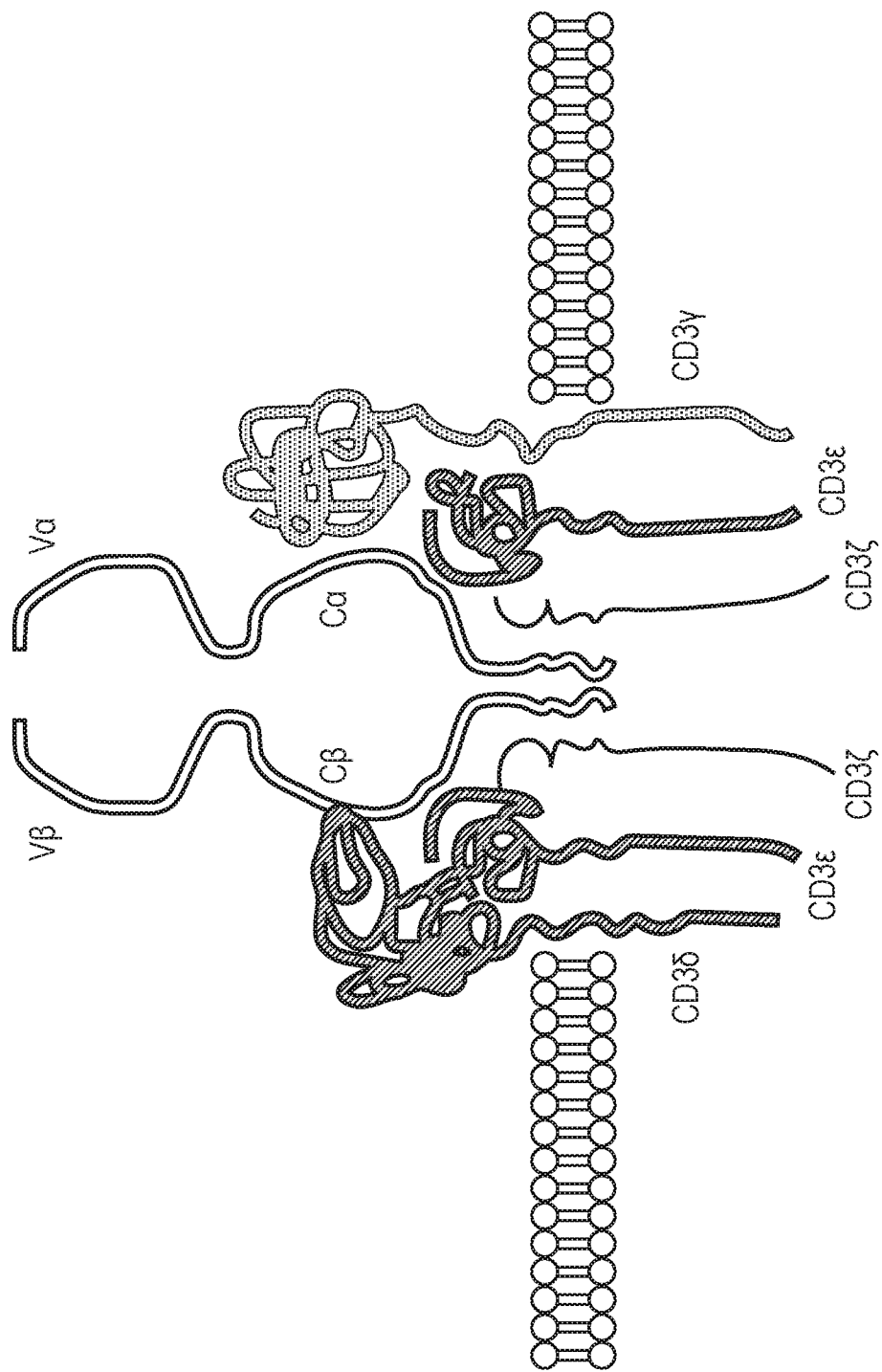

Specification includes a Sequence Listing.

(56) References Cited

FOREIGN PATENT DOCUMENTS

| WO | WO-2017/072361 A1 | 5/2017 |
|----|---|---|
| WO | WO-2017/127499 A1 | 7/2017 |
| WO | WO-2017/127664 A1 | 7/2017 |
| WO | WO-2017/142928 A1 | 8/2017 |
| WO | WO-2017/156479 A1 | 9/2017 |
| WO | WO-2018/011138 A1 | 1/2018 |
| WO | WO-2018/119314 A1 | 6/2018 |
| WO | WO-2018/217799 A1 | 11/2018 |
| WO | WO-2018/237335 A1 | 12/2018 |
| WO | WO-2019/005636 A2 | 1/2019 |
| WO | WO-2019/005638 A2 | 1/2019 |
| WO | WO-2019/016381 A1 | 1/2019 |
| WO | WO-2019/030223 A1 | 2/2019 |
| WO | WO-2019/030240 A1 | 2/2019 |
| WO | WO-2019/090110 A1 | 5/2019 |
| WO | WO-2019/122445 A1 | 6/2019 |
| WO | WO-2019/122447 A1 | 6/2019 |
| WO | WO-2019/225992 A1 | 11/2019 |

OTHER PUBLICATIONS

Gohil et al., Novel Humanised ROR1 Chimeric Antigen Receptors for the Treatment of Haematological Malignancies, Blood (Dec. 2, 2016), 128(22):3361, 703. Adoptive Immunotherapy Poster II (<http://doi.org/10.1182/blood.V128.22.3361.3361>).

Barat, B. et al., Development of a Humanized ROR1 x CD3 Bispecific DART Molecule for the Treatment of Solid and Liquid Tumors, presented at the 2016 American Association for Cancer Research Annual Meeting, one page, Apr. 16-20, 2016.

Baskar, S. et al., Targeting malignant B cells with an immunotoxin against ROR1, mAbs, 4:3, 349-361 (2012).

Daneshmanesh, A. et al., Monoclonal antibodies against ROR1 induce apoptosis of chronic lymphocytic leukemia (CLL) cells, Leukemia, 26:1348-1355 (2012).

Deniger, D. et al., Sleeping Beauty Transposition of Chimeric Antigen Receptors Targeting Receptor Tyrosine Kinase-Like Orphan Receptor-1 (ROR1) into Diverse Memory T-Cell Populations, PLOS One, 10(6): 19 pages (2015).

Gohil, S. et al., An ROR1 bi-specific T-cell engager provides effective targeting and cytotoxicity against a range of solid tumors, Oncoimmunology, 6(7):e1326437, 11 pages (2017).

Gohil, S. et al., Preclinical development of novel humanised ROR1 targeting chimeric antigen receptor T cells and bispecific T-cell engagers, Poster Abstracts, one page (2017).

Hudecek, M. et al., Receptor Affinity and Extracellular Domain Modifications Affect Tumor Recognition by ROR1-Specific Chimeric Antigen Receptor T Cells, Clinical Cancer Research, 19(12):3153-3164 (2013).

Kershaw, M. et al., A Phase I Study on Adoptive Immunotherapy Using Gene-Modified T Cells for Ovarian Cancer, Clinical Cancer Research, 12:6106-6115 (2006).

Lamers, C. et al., Process validation and clinical evaluation of a protocol to generate gene-modified T lymphocytes for umunogene therapy for metastatic renal cell carcinoma: GMP-controlled transduction and expansion of patient's T lymphocytes using a carboxy anhydrase IX-specific scFv transgene, Cytotherapy, 8(6):542-553 (2006).

Maus, M. et al., T Cells Expressing Chimeric Antigen Receptors Can Cause Anaphylaxis in Humans, Cancer Immunology Research, 1(1):26-31 (2013).

Paredes-Moscosso, S. et al., Novel ROR1 Antibody Is Able to Trigger Specific and Superior Complemente-Dependent Cytotoxicity (CDC) on Primary CLL Cells, Blood, 128(22):2052, 4 pages (2016).

Paredes-Moscosso, Solange Rosa, ROR1 as a Target for Cancer Immunotherapy, A thesis submitted to University College London (UCL) for the degree of Doctor of Philosophy, 305 pages (2017).

* cited by examiner

Cytotoxicity of novel ScFv based CAR T-Cells with CD8 spacer

ROR1 CAR T-CELLS

The invention relates to a chimeric antigen receptor (CAR) which comprises an antigen binding domain which selectively binds to Receptor Tyrosine Kinase Like Orphan Receptor 1 (ROR1), and its use.

BACKGROUND OF THE INVENTION

Receptor Tyrosine Kinase Like Orphan Receptor 1 (ROR1) (also known as Neurotrophic Tyrosine Kinase, Receptor-Related 1, NTRKR1) is an onco-foetal antigen expressed during embryogenesis but with limited expression on normal adult tissue. It is however expressed on a number of haematological and solid malignancies: Chronic Lymphocytic Leukaemia (CLL), Acute Lymphoblastic Leukaemia (ALL), Mantle Cell Leukaemia, Hairy Cell Leukaemia, Pancreatic cancer, Prostate cancer, colon cancer, bladder cancer, ovarian cancer, glioblastoma, testicular cancer, uterine cancer, adrenal cancer, breast cancer, lung cancer, melanoma, neuroblastoma, sarcoma, renal cancer. Furthermore, ROR1 is expressed on a subset of cancer stem cells.

Recently, T cells have been genetically engineered to express artificial T cell receptors on their surface called chimeric antigen receptors, or CARs. CARs are proteins that allow T cells to recognize a specific, pre-selected protein, or antigen, found on targeted tumour cells. CAR-T cells can be cultured and expanded in the laboratory, then re-infused into a patient. Through the guidance of the engineered T cell receptor, CAR-T cells recognize and destroy the cancer cells that display the specific antigen on their surfaces. In 2014, the first chimeric antigen receptor T (CAR-T) cell-based immunotherapy, known as CTL019, received breakthrough drug designation from the US Food and Drug Administration for the treatment of relapsed and refractive acute lymphoblastic leukaemia (ALL) and has gone on to be used in CLL, lymphoma and myeloma.

Although CD19 based CAR-T cells have shown great promise in the clinic in early phase trials, these also target the normal B cell clones resulting in B cell aplasia and prolonged hypogammaglobulinemia, something which would not occur with ROR1. Furthermore, most CAR-T cells target disease specific antigens and therefore a limited range of tumours, whilst ROR1 is able to target a broad range of malignancies both haematological and solid.

The present inventors have identified ROR1 as an attractive therapeutic target and generated CAR-T cells which specifically bind to ROR1 and can be used to treat the aforementioned cancers.

SUMMARY OF THE INVENTION

A first aspect of the invention relates to a chimeric antigen receptor (CAR) which comprises an antigen binding domain which selectively binds to Receptor Tyrosine Kinase Like Orphan Receptor 1 (ROR1), wherein the antigen binding domain binds to an epitope of ROR1 comprising amino acid Gln-261.

In a first embodiment, the antigen binding domain comprises a light chain variable domain and a heavy chain variable domain, wherein the light chain variable domain comprises a light chain complementarity determining region (LCDR)1, an LCDR2 and an LCDR3, wherein LCDR1 comprises the amino acid sequence set forth in SEQ ID NO: 16; LCDR2 comprises the amino acid sequence set forth in SEQ ID NO: 18; and LCDR3 comprises the amino acid sequence set forth in SEQ ID NO: 20; and wherein the heavy chain variable domain comprises a heavy chain complementarity determining region (HCDR)1, an HCDR2 and an HCDR3, wherein HCDR1 comprises the amino acid sequence set forth in SEQ ID NO: 23; HCDR2 comprises the amino acid sequence set forth in SEQ ID NO: 25; and HCDR3 comprises the amino acid sequence set forth in SEQ ID NO: 57; wherein the sequence of each complementarity determining region may differ from the given sequence at up to two amino acid positions.

Furthermore, the invention relates to an isolated nucleic acid molecule encoding the disclosed CAR.

The present invention also relates to a cell, preferably a T cell, which comprises the disclosed CAR and methods for making such cells. Alternatively, the cell can be a NK cell, gamma delta T cell or an iPS cell.

The invention further relates to a cell comprising the disclosed CAR for use in the treatment of cancer in a subject wherein the cell comprising the ROR1 selective CAR is administered to the subject to cause selective depletion of malignant cells. Further aspects of the invention are related to a method of treating cancer.

DETAILED DESCRIPTION

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Unless otherwise explained, all technical and scientific terms used herein have the same meaning as commonly understood by one of ordinary skill in the art to which this disclosure belongs.

Administration: The introduction of a composition into a subject by a chosen route. Administration can be local or systemic. For example, if the chosen route is intravenous, the composition is administered by introducing the composition into a vein of the subject. For example, administration can be by oral and parenteral routes, intraperitoneally, intravenously, subcutaneously, transcutaneously, intramuscularly, or via local delivery for example by catheter or stent. In some examples a CAR specific for a ROR1 polypeptide, is administered to a subject. Typically, a physician will determine the actual dosage which will be most suitable for an individual subject and it will vary with the age, weight and response of the particular patient. The dosage is such that it is sufficient to reduce or deplete the number of malignant cells.

Agent: Any substance or any combination of substances that is useful for achieving an end or result; for example, a substance or combination of substances useful for preventing or treating cancer. Agents include, and are not limited to, proteins, nucleic acid molecules, compounds, small molecules, organic compounds, inorganic compounds, or other molecules of interest. An agent can include a therapeutic agent (such as an anti-viral agent), a diagnostic agent or a pharmaceutical agent. In some embodiments, the agent is a CAR, or a cell comprising a CAR. The skilled artisan will understand that particular agents may be useful to achieve more than one result.

Amino acid substitution: The replacement of one amino acid in a peptide with a different amino acid.

Amplification: A technique that increases the number of copies of a nucleic acid molecule (such as an RNA or DNA). An example of amplification is the polymerase chain reaction, in which a biological sample is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in PCT Publication No. WO 90/01069; ligase chain reaction amplification, as disclosed in European Patent Publication EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide substantially encoded by an immunoglobulin gene or immunoglobulin genes, or antigen binding fragments thereof, which specifically binds and recognizes an analyte (antigen) such as a ROR1 polypeptide, or an immunogenic fragment thereof. Immunoglobulin genes include the kappa, lambda, alpha, gamma, delta, epsilon and mu constant region genes, as well as the myriad immunoglobulin variable region genes.

Antibodies exist, for example, as intact immunoglobulins and as a number of well characterised fragments produced by digestion with various peptidases. For instance, Fabs, Fvs, scFvs that specifically bind to a ROR1 polypeptide, or fragments of this polypeptide, are specific binding agents. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies and heteroconjugate antibodies such as bispecific antibodies. See also, *Pierce Catalog and Handbook,* 1994-1995 (Pierce Chemical Co., Rockford, Ill.); Kuby, *Immunology,* 3rd Ed., W.H. Freeman & Co., New York, 1997.

Antibody fragments include, but are not limited to, the following: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')2, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule.

Antigen binding fragments of an antibody can be produced by the modification of whole antibodies or those synthesized de novo using recombinant DNA methodologies. In some examples, the term antibody includes the amino acid sequences of one or more of the CDRs from the antibody grafted onto a scaffold.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. The disclosed antibodies can be class switched.

Each heavy and light chain contains a constant region and a variable region, (the regions are also known as "domains"). In several embodiments, the heavy and the light chain variable domains combine to specifically bind the antigen. In additional embodiments, only the heavy chain variable domain is required. For example, naturally occurring camelid antibodies consisting of a heavy chain only are functional and stable in the absence of light chain (see, e.g., Hamers-Casterman et al., *Nature,* 363:446-448, 1993; Sheriff et al., *Nat. Struct. Biol.,* 3:733-736, 1996). Light and heavy chain variable domains contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for antigen binding. The sequences of the framework regions of different light or heavy chains are relatively conserved within a species. The framework region of an antibody, that is the combined framework regions of the constituent light and heavy chains, serves to position and align the CDRs in three-dimensional space.

The CDRs of each chain are typically referred to as CDR1, CDR2, and CDR3 (from the N-terminus to C-terminus), and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Light chain CDRs can also be referred to as CDR L1, CDR L2 and CDR L3, or LCDR1, LCDR2 and LCDR3. Heavy chain CDRs can be referred to as CDR H1, CDR H2 and CDR H3, or HCDR1, HCDR2 and HCDR3.

References to "$V_H$" or "VH" refer to the variable region of an immunoglobulin heavy chain, including that of an antibody fragment, such as Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas". In some embodiments, monoclonal antibodies can be humanized monoclonal antibodies. In some embodiments, monoclonal antibodies can be chimeric antibodies. In some examples monoclonal antibodies are isolated from a subject. The amino acid sequences of such isolated monoclonal antibodies can be determined.

A "humanised" antibody is an antibody including a human framework region and one or more CDRs from a non-human (such as a chimpanzee, mouse, rat, or synthetic) immunoglobulin. The non-human antibody providing the CDRs is termed a "donor", and the human antibody providing the framework is termed an "acceptor". In one embodiment, all the CDRs are from the donor antibody in a humanised antibody. Constant regions need not be present, but if they are, they must be substantially identical to human antibody constant regions, such as at least about 85-90%, such as about 95% or more identical. Hence, all parts of a humanised antibody, except possibly the CDRs, are substantially identical to corresponding parts of natural human antibody sequences. A "humanised antibody" can include a humanised light chain and a humanised heavy chain. A humanised antibody binds to the same antigen as the donor antibody that provides the CDRs. The acceptor framework of a humanised antibody may have a limited number of substitutions by amino acids taken from the donor framework. Humanised or other monoclonal antibodies can have additional conservative amino acid substitutions which have substantially no effect on antigen binding or other immunoglobulin functions. Humanised immunoglobulins can be constructed by means of genetic engineering (for example, see U.S. Pat. No. 5,585,089). Preferably, the antibodies of the present invention are humanised.

A "chimeric" antibody is an antibody which includes sequences from two different antibodies, which typically are of different species. For example, a chimeric antibody may comprise heavy and light chain variable regions derived from a first species and heavy and light chain constant regions derived from a second species. The variable and constant regions of the light chain may be derived from a first species while the variable region of the heavy chain may be derived from the first species and the constant region of the heavy chain is derived from a second species.

A "neutralizing antibody" is an antibody which reduces effect of a virus, bacteria or tumour for example, by binding to a specific antigen on the virus, bacteria or tumour. In some examples, an antibody, or CAR that s specific for a ROR1 neutralizes the effect of the tumour.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous antigens, such as the disclosed antigens. "Epitope" or "antigenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance.

Examples of antigens include, but are not limited to, peptides, lipids, polysaccharides, and nucleic acids containing antigenic determinants, such as those recognized by an immune cell. Antigens can include peptides derived from a pathogen of interest or from a cancerous cell. Exemplary pathogens include bacteria, fungi, viruses and parasites. In some embodiments, an antigen is derived from a cancerous cell such as a haematological cancerous cell (chronic lymphocytic leukaemia—CLL, acute lymphoblastic leukaemia, mantle cell lymphoma) or a solid malignancy (breast, pancreatic, melanoma). In some embodiments, the antigen is a ROR1 polypeptide or antigenic fragment thereof.

A "target epitope" is a specific epitope on an antigen that specifically binds an antibody of interest, such as a monoclonal antibody. In some examples, a target epitope includes the amino acid residues that contact the antibody or CAR of interest, such that the target epitope can be selected by the amino acid residues determined to be in contact with the antibody or CAR.

Binding affinity: Affinity of an antibody, antigen binding fragment or CAR thereof for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1\times10^{-9}$ M. In other embodiments, a high binding affinity is at least about $1.5\times 10'$, at least about $2\times10^{-9}$, at least about $3\times10^{-9}$, at least about $4\times10^{-9}$, or at least about $5\times10^{-9}$ M.

Cell: The present invention also relates to a cell, such as an immune cell, comprising a CAR. The cell may comprise a nucleic acid or a vector of the present invention. The cell may be a T cell or a natural killer (NK) cell. The cell may also be an iPS generated cell or a gamma delta T-cell.

The T cell may be a T cell or T lymphocyte which are a type of lymphocyte that play a central role in cell-mediated immunity. They can be distinguished from other lymphocytes, such as B cells and natural killer cells (NK cells), by the presence of a T cell receptor (TCR) on the cell surface. There are various types of T cell, as summarized below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of CD4+ Treg cells have been described: naturally occurring Treg cells and adaptive Treg cells. Naturally occurring Treg cells (also known as CD4+CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX. Adaptive Treg cells (also known as Tr1 cells or Th3 cells) may originate during a normal immune response.

The cell may be a Natural Killer cell (or NK cell). NK cells form part of the innate immune system. NK cells provide rapid responses to innate signals from virally infected cells in an MHC independent manner. NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CAR cells of the invention may be any of the cell types mentioned above.

T or NK cells expressing a CAR according to the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, T or NK cells expressing a CAR according to invention may be derived from ex vivo differentiation of inducible progenitor cells or embryonic progenitor cells to T or NK cells. Alternatively, an immortalized T-cell line which retains its lytic function and could act as a therapeutic may be used.

In all these embodiments, CAR cells are generated by introducing DNA or RNA coding for the CAR by one of many means including transduction with a viral vector, transfection with DNA or RNA.

The CAR cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding a CAR according to the first aspect of the invention, for example by treatment with an anti-CD3 monoclonal antibody.

The T or NK cell of the invention may be made by:
(i) isolation of a T or NK cell-containing sample from a subject or other sources listed above; and
(ii) transduction or transfection of the T or NK cells with a nucleic acid sequence(s) encoding a CAR of the invention.

The T or NK cells may then by purified, for example, selected on the basis of expression of the antigen-binding domain of the antigen-binding polypeptide.

This disclosure may also provide a kit which comprises a T or NK cell comprising a CAR according to the invention.

Chimeric Antigen Receptor (CAR): Chimeric antigen receptors (CARs), also known as chimeric T cell receptors, artificial T cell receptors and chimeric immunoreceptors, are engineered receptors, which graft an arbitrary specificity onto an immune effector cell. In a classical CAR, the specificity of a monoclonal antibody is grafted onto a T cell. CAR-encoding nucleic acids may be transferred to T cells using, for example, retroviral vectors. In this way, a large number of cancer-specific T cells can be generated for adoptive cell transfer.

The target antigen binding domain of a CAR is commonly fused via a spacer and transmembrane domain to an endodomain, which comprises or associates with an intracellular T cell signalling domain. When the CAR binds the target antigen, this results in the transmission of an activating signal to the T cell it is expressed on.

The CAR may also comprise a transmembrane domain which spans the membrane. It may comprise a hydrophobic alpha helix. The transmembrane domain may be derived from CD28, which gives good receptor stability.

The endodomain is the portion of the CAR involved in signal-transmission. The endodomain either comprises or associates with an intracellular T cell signalling domain. After antigen recognition, receptors cluster and a signal is transmitted to the cell. The most commonly used T cell signalling component is that of CD3-zeta which contains 3 ITAMs (Immunoreceptor tyrosine-based activation motifs). This transmits an activation signal to the T cell after antigen is bound. CD3-zeta may not provide a fully competent activation signal and additional co-stimulatory signalling may be needed. For example, chimeric CD28, and OX40 can be used with CD3-Zeta to transmit a proliferative/survival signal, or all three can be used together. Alternatively, 41BB can be used with CD3-Zeta. However, a skilled person will appreciate that any suitable co-stimulatory domains can be used.

The endodomain of the CAR may comprise the CD28 endodomain and OX40 and CD3-Zeta endodomain. Alternatively, the endodomain of the CAR may comprise 41BB and CD3-Zeta endodomain.

The CAR may comprise a signal peptide so that when the CAR is expressed inside a cell, such as a T cell, the nascent protein is directed to the endoplasmic reticulum and subsequently to the cell surface, where it is expressed.

The CAR may comprise a spacer sequence to connect the ROR1-binding domain with the transmembrane domain and spatially separate the ROR1-binding domain from the endodomain. A flexible spacer allows the ROR1-binding domain to orient in different directions to enable ROR1 binding. A skilled person will appreciate that any suitable spacer sequence can be used.

The spacer sequence may, for example, comprise a short flexible linker, an IgG1 Fc region, an IgG1 hinge or a CD8 stalk, or a combination thereof. The linker may alternatively comprise an alternative linker sequence which has similar length and/or domain spacing properties as an IgG1 Fc region, an IgG1 hinge or a CD8 stalk.

Clonal variant: Any sequence, which differs by one or more nucleotides or amino acids, in presence of V region with identical mutations compared to the germline, identical VDJ or VJ gene usage, and identical D and J length. The "germline" sequence is intended to be the sequence coding for the antibody/immunoglobulin (or of any fragment thereof) deprived of mutations, for example somatic mutations. The percentage of homology represents an indication of the mutational events which any type of heavy chain portion undergoes after contact with an antigen.

Conjugate: A complex of two molecules linked together, for example, linked together by a covalent bond. In one embodiment, a CAR may be linked to an effector molecule; for example, an antigen binding domain that specifically binds to a ROR1 polypeptide, covalently linked to an effector molecule or to a toxin. The linkage can be by chemical or recombinant means. In one embodiment, the linkage is chemical, wherein a reaction between the antigen binding domain and the effector molecule has produced a covalent bond formed between the two molecules to form one molecule. A peptide linker (short peptide sequence) can optionally be included between the antigen binding domain and the effector molecule. Because conjugates can be prepared from two molecules with separate functionalities, such as a CAR and an effector molecule, they are also sometimes referred to as "chimeric molecules." In one embodiment, antigen binding domain linked to an effector molecule may be further joined to a lipid or other molecule to a protein or peptide to increase its half-life in the body.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antigen binding domain. Contacting can also include contacting a cell for example by placing a CAR in direct physical association with a cell.

Control: A reference standard. In some embodiments, the control is a sample obtained from a healthy patient. In other embodiments, the control is a tissue sample obtained from a patient diagnosed with cancer that serves as a positive control. In still other embodiments, the control is a historical control or standard reference value or range of values (such as a previously tested control sample, such as a group of infected patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Non-limiting examples of detectable markers include fluorophores, fluorescent proteins, chemiluminescent agents, enzymatic linkages, radioactive isotopes and heavy metals or compounds (for example super paramagnetic iron oxide nanocrystals for detection by MRI). In one example, a "labelled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labelling polypeptides and glycoproteins are known in the art and may be used. Examples of labels for polypeptides include, but are not limited to, the following: radioisotopes or radionuclides (such as $^{35}$S or $^{131}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998). In particular embodiments of the invention, the antigen binding domain or fragment thereof can be labelled with a detectable marker.

Detecting: To identify the existence, presence, or fact of something. General methods of detecting are known to the skilled artisan (see, for example, U.S. Pat. No. 7,635,476) and may be supplemented with the protocols and reagents disclosed herein.

Epitope: An antigenic determinant. These are particular chemical groups or peptide sequences on a molecule that are antigenic, i.e. that elicit a specific immune response. An antigen binding domain or antibody specifically binds a particular antigenic epitope on a polypeptide. In some examples a disclosed antigen binding domain specifically binds to an epitope on the surface of ROR1.

Framework Region: Amino acid sequences interposed between CDRs. The term includes variable light and variable heavy framework regions. The framework regions serve to hold the CDRs in an appropriate orientation for antigen binding.

Fc polypeptide: The polypeptide comprising the constant region of an antibody excluding the first constant region immunoglobulin domain. Fc region generally refers to the last two constant region immunoglobulin domains of IgA, IgD, and IgG, and the last three constant region immunoglobulin domains of IgE and IgM. An Fc region may also include part or all of the flexible hinge N-terminal to these domains. For IgA and IgM, an Fc region may or may not comprise the tailpiece, and may or may not be bound by the J chain. For IgG, the Fc region comprises immunoglobulin domains Cgamma2 and Cgamma3 (Cγ2 and Cγ3) and the lower part of the hinge between Cgamma1 (Cγ1) and Cγ2. Although the boundaries of the Fc region may vary, the human IgG heavy chain Fc region is usually defined to comprise residues C226 or P230 to its carboxyl-terminus, wherein the numbering is according to the EU index. For IgA, the Fc region comprises immunoglobulin domains Calpha2 and Calpha3 (Cα2 and Cα3) and the lower part of the hinge between Calpha1 (Cα1) and Cα2. Encompassed within the definition of the Fc region are functionally equivalent analogs and variants of the Fc region. A functionally equivalent analog of the Fc region may be a variant Fc region, comprising one or more amino acid modifications relative to the wild-type or naturally existing Fc region. Variant Fc regions will possess at least 50% homology with a naturally existing Fc region, such as about 80%, and about 90%, or at least about 95% homology. Functionally equivalent analogs of the Fc region may comprise one or more amino acid residues added to or deleted from the N- or C-termini of the protein, such as no more than 30 or no more than 10 additions and/or deletions. Functionally equivalent analogs of the Fc region include Fc regions operably linked to a fusion partner. Functionally equivalent analogs of the Fc region must comprise the majority of all of the Ig domains that compose Fc region as defined above; for example IgG and IgA Fc regions as defined herein must comprise the majority of the sequence encoding $CH_2$ and the majority of the sequence encoding $CH_3$. Thus, the $CH_2$ domain on its own, or the $CH_3$ domain on its own, are not considered Fc region. The Fc region may refer to this region in isolation, or this region in the context of an Fc fusion polypeptide.

Host cells: Cells in which a vector can be propagated and its DNA expressed, for example a disclosed CAR can be expressed in a host cell. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune complex: The binding of antibody to a soluble antigen forms an immune complex. The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography. Immunological binding properties of selected antibodies may be quantified using methods well known in the art.

Immunologically reactive conditions: Includes reference to conditions which allow an antibody or antigen binding domain raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Inhibiting or treating a disease: Inhibiting the full development of a disease or condition, for example, in a subject who is at risk for cancer. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in size of the tumour/cancer, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a cell, for example a B-cell, a nucleic acid, peptide, protein, heavy chain domain or antibody) has been substantially separated, produced apart from, or purified away from other biological components in the cell of the organism in which the component naturally occurs, such as, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides, and proteins prepared by recombinant expression in a host cell as well as chemically synthesized nucleic acids.

$K_d$: The dissociation constant for a given interaction, such as a polypeptide ligand interaction or an antibody antigen interaction. For example, for the bimolecular interaction of an antigen binding domain or antibody (such as any of the antigen binding domains disclosed herein) and an antigen (such as a ROR1 polypeptide) it is the concentration of the individual components of the bimolecular interaction divided by the concentration of the complex.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In some examples, a disclosed CAR may be labeled.

Malignant Cells: The term 'malignant' is used herein according to its standard meaning to refer to a cell which is not self-limited in its growth, may be capable of invading into adjacent tissues and may be capable of spreading to distant tissue.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, CABIOS 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

ClustalW is a program that aligns three or more sequences in a computationally efficient manner. Aligning multiple sequences highlights areas of similarity which may be associated with specific features that have been more highly conserved than other regions. Thus, this program can classify sequences for phylogenetic analysis, which aims to model the substitutions that have occurred over evolution and derive the evolutionary relationships between sequences. The ClustalW multiple sequence alignment web form is available on the internet from EMBL-EBI (ebi.ac.uk/Tools/msa/clustalw2/), see also Larkin et al., *Bioinformatics* 2007 23(21): 2947-2948.

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences.

The nucleotides can be ribonucleotides, deoxyribonucleotides, or modified forms of either nucleotide. The term includes single- and double-stranded forms of DNA.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the cells and CARs herein disclosed.

In general, the nature of the carrier will depend on the particular mode of administration being employed. For instance, parenteral formulations usually comprise injectable fluids that include pharmaceutically and physiologically acceptable fluids, which include, but are not limited to, water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. In some examples a pharmaceutical agent includes one or more of the disclosed cells expressing a CAR according to the invention.

Polypeptide: Any chain of amino acids, regardless of length or post-translational modification (e.g., glycosylation or phosphorylation). In one embodiment, the polypeptide is a ROR1 polypeptide. In one embodiment, the polypeptide is a disclosed antibody or a fragment thereof. A "residue" refers to an amino acid or amino acid mimetic incorporated in a polypeptide by an amide bond or amide bond mimetic. A polypeptide has an amino terminal (N-terminal) end and a carboxy terminal end. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50% of the total peptide or protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of polypeptide sequences for comparison are well known in the art. Various programs and alignment algorithms may be used as described above. Altschul et al., *Nature Genet.* 6:119, 1994, presents a detailed consideration of sequence alignment methods and homology calculations. The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet (along with a description of how to determine sequence identity using this program).

Homologs and variants of a $V_L$ or a $V_H$ of an antigen binding domain that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. One of skill in the art will appreciate that these sequence identity ranges are provided for guidance only; it is entirely possible that strongly significant homologs could be obtained that fall outside of the ranges provided.

Nucleic acids that "selectively hybridise" or "selectively bind" do so under moderately or highly stringent conditions that excludes non-related nucleotide sequences. In nucleic acid hybridisation reactions, the conditions used to achieve a particular level of stringency will vary, depending on the nature of the nucleic acids being hybridised. For example, the length, degree of complementarity, nucleotide sequence composition (for example, GC v. AT content), and nucleic acid type (for example, RNA versus DNA) of the hybridising regions of the nucleic acids can be considered in selecting hybridisation conditions. An additional consideration is whether one of the nucleic acids is immobilised, for example, on a filter.

A specific example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual,* 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed.

However, as mentioned above, optimal conditions will vary, depending on the particular hybridization reaction involved, and can be determined empirically.

Specifically bind: When referring to an antibody or antigen binding domain, refers to a binding reaction which determines the presence of a target protein, peptide, or polysaccharide in the presence of a heterogeneous population of proteins and other biologics. Thus, under designated conditions, an antibody or antigen binding domain binds preferentially to a particular target protein, peptide or polysaccharide (such as an antigen present on the surface of a tumour, for example ROR1) and do not bind in a significant amount to other proteins or polysaccharides present in the sample or subject. Specific binding can be determined by methods known in the art. With reference to an antibody antigen complex, specific binding of the antigen and antibody has a $K_d$ of less than about $10^{-7}$ Molar, such as less than about $10^{-7}$ Molar, $10^{-8}$ Molar, $10^{-9}$, or even less than about $10^{-10}$ Molar.

T Cell Receptor (TCR): The T cell receptor (TCR) is expressed on the surface of T lymphocytes and is responsible for recognizing antigens bound to major histocompatibility complex (MHC) molecules. When the TCR engages with antigenic peptide and MHC (peptide/MHC), the T lymphocyte is activated through a series of biochemical events mediated by associated enzymes, co-receptors, specialized adaptor molecules, and activated or released transcription factors.

The TCR is a disulfide-linked membrane-anchored heterodimer normally consisting of the highly variable alpha (α) and beta (β) chains expressed as part of a complex with the invariant CD3 chain molecules. T cells expressing this receptor are referred to as α:β (or αβ) T cells (~95% total T cells). A minority of T cells express an alternate receptor, formed by variable gamma (γ) and delta (δ) chains, and are referred to as γδ T cells (~5% total T cells).

Each α and β chain is composed of two extracellular domains: a Variable (V) region and a Constant (C) region, both of Immunoglobulin superfamily (IgSF) domain forming antiparallel β-sheets. The constant region is proximal to the cell membrane, followed by a transmembrane region and a short cytoplasmic tail, while the variable region binds to the peptide/MHC complex (see FIG. 1). The constant region of the TCR consists of short connecting sequences in which a cysteine residue forms disulfide bonds, which forms a link between the two chains.

The variable domains of both the TCR α-chain and β-chain have three hypervariable or complementarity determining regions (CDRs). The variable region of the β-chain also has an additional area of hypervariability (HV4), however, this does not normally contact the antigen and is therefore not considered a CDR.

The TCR also comprises up to five invariant chains γ,δ,ε (collectively termed CD3) and ζ. The CD3 and ζ subunits mediate TCR signalling through specific cytoplasmic domains which interact with second-messenger and adapter molecules following the recognition of the antigen by αβ or γδ. Cell surface expression of the TCR complex is preceded by the pair-wise assembly of subunits in which both the transmembrane and extracellular domains of TCR α and β and CD3 γ and δ play a role.

TCRs are therefore commonly composed of the CD3 complex and the TCR α and β chains, which are in turn composed of variable and constant regions (FIG. 1).

Therapeutic agent: Used in a generic sense, it includes treating agents, prophylactic agents, and replacement agents.

Therapeutically effective amount or effective amount: A quantity of a specific substance, such as a disclosed antibody, sufficient to achieve a desired effect in a subject being treated. For instance, this can be the amount necessary to inhibit tumour growth. In several embodiments, a therapeutically effective amount is the amount necessary to reduce a symptom of the disease. When administered to a subject, a dosage will generally be used that will achieve target tissue concentrations that has been shown to achieve a desired in vitro effect.

Vector: A nucleic acid molecule may be introduced into a host cell by a vector, thereby producing a transformed host cell. A vector may include nucleic acid sequences that permit it to replicate in a host cell, such as an origin of replication. A vector may also include one or more selectable marker genes and other genetic elements known in the art. The vector may, for example, be a plasmid or a viral vector, such as a retroviral vector or a lentiviral vector, or a transposon based vector or synthetic mRNA. The vector may be capable of transfecting or transducing a T cell or a NK cell.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below.

The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Chimeric Antigen Receptors (CARs) that Specifically Bind to ROR1

Clinically useful CARs that comprise an antigen binding domain that selectively binds to ROR1 are disclosed herein.

In some embodiments the antigen binding domain specifically binds a ROR1 polypeptide with an equilibrium constant ($K_d$) of 6 nM or less. In several embodiments, the antigen binding domain binds the ROR1 polypeptide with a $K_D$ of about $1.6 \times 10^{-9}$M or less, about $2 \times 10^{-9}$M or less, about $3 \times 10^{-9}$ M or less, about $4 \times 10^{-9}$ M or less or about $5 \times 10^{-9}$M or less.

The antigen binding domains disclosed herein can be derived from rat antibodies, and can include a rat framework region. In some preferred embodiments, the antigen binding domains are humanised, and thus include one or more human framework regions. In some embodiments, the antigen binding domains disclosed herein are chimeric. In some embodiments, the antigen binding domains include rat and human regions.

The antigen binding domain can specifically bind a ROR1 polypeptide. Preferably, the antigen binding domain can specifically bind a human ROR1 polypeptide. The antigen binding domain preferably comprises a heavy chain and a light chain and preferably each VH and VL is composed of three CDRs and four FWRs, arranged from amino-terminus to carboxy-terminus in the following order: FWR1, CDR1, FWR2, CDR2, FWR3, CDR3, FWR4 as described above.

In a first embodiment, the antigen binding domain comprises a light chain variable domain and a heavy chain variable domain, wherein the light chain variable domain comprises a light chain complementarity determining region (LCDR)1, an LCDR2 and an LCDR3, wherein LCDR1 comprises the amino acid sequence set forth in SEQ ID NO: 16; LCDR2 comprises the amino acid sequence set forth in SEQ ID NO: 18; and LCDR3 comprises the amino acid sequence set forth in SEQ ID NO: 20; and wherein the heavy chain variable domain comprises a heavy chain complementarity determining region (HCDR)1, an HCDR2 and an HCDR3, wherein HCDR1 comprises the amino acid sequence set forth in SEQ ID NO: 23; HCDR2 comprises the amino acid sequence set forth in SEQ ID NO: 25; and HCDR3 comprises the amino acid sequence set forth in SEQ ID NO: 57; wherein the sequence of each complementarity determining region may differ from the given sequence at up to two amino acid positions.

The sequence of each CDR may differ from the given sequence at up to two amino acid positions. This means that the CDR may contain one or two amino acid substitutions compared to the given sequence. However, if one or more of the CDRs does contain amino acid substitutions, the CAR can still selectively bind to ROR1. Preferably, the amino acid substitutions are conservative substitutions.

Preferably, the sequence of each CDR may differ from the given sequence at one amino acid position. This means that the CDR may contain one amino acid substitution compared to the given sequence. Preferably, the amino acid substitution is a conservative substitution.

In some embodiments, heavy chain complementarity determining region 3 (HCDR3) comprises an amino acid sequence selected from any of the sequences set forth in SEQ ID NOs: 27, 36, 44 and 49. Preferably, HCDR3 comprises an amino acid sequence selected from any of the sequences set forth in SEQ ID NOs: 36, 44 and 49.

The antigen binding domain may have a light chain variable domain which comprises a Light Chain Framework Region (LCFR)1 comprising the amino acid sequence as set forth as one of SEQ ID NOs: 15, 29, 50 and 53; an LCFR2 comprising the amino acid sequence as set forth as one of SEQ ID NOs: 17, 30, 38 and 46; an LCFR3 comprising the amino acid sequence as set forth as one of SEQ ID NOs: 19, 31, 39, 47 and 54; and an LCFR4 comprising the amino acid sequence as set forth as one of SEQ ID NOs: 21, 32 and 40.

Preferably, the antigen binding domain has a light chain variable domain which comprises an LCFR1 comprising the amino acid sequence as set forth as one of SEQ ID NOs: 29, 50 and 53; an LCFR2 comprising the amino acid sequence as set forth as one of SEQ ID NOs: 30, 38 and 46; an LCFR3 comprising the amino acid sequence as set forth as one of SEQ ID NOs: 31, 39, 47 and 54; and an LCFR4 comprising the amino acid sequence as set forth as one of SEQ ID NOs: 32 and 40.

The antigen binding domain may have a heavy chain variable domain which comprises a Heavy Chain Framework Region (HCFR)1 comprising the amino acid sequence as set forth as one of SEQ ID NOs: 22, 33, 41 and 55; an HCFR2 comprising the amino acid sequence as set forth as one of SEQ ID NOs: 24, 34, 42 and 51; an HCFR3 comprising the amino acid sequence as set forth as one of SEQ ID NOs: 26, 35, 43, 48, 52 and 56; and an HCFR4 comprising the amino acid sequence as set forth as one of SEQ ID NOs: 28, 37 and 45.

Preferably, the antigen binding domain may have a heavy chain variable domain which comprises an HCFR1 comprising the amino acid sequence as set forth as one of SEQ ID NOs: 33, 41 and 55; an HCFR2 comprising the amino acid sequence as set forth as one of SEQ ID NOs: 34, 42 and 51; an HCFR3 comprising the amino acid sequence as set forth as one of SEQ ID NOs: 35, 43, 48, 52 and 56; and an HCFR4 comprising the amino acid sequence as set forth as one of SEQ ID NOs: 37 and 45.

As indicated below, the sequence of each framework region referred to above may differ from the given sequence. For example, it may differ at up to 10 amino acid positions, although it is preferred that fewer than 10 amino acid substitutions are present so that there may be up to 9, 8, 7, 6, 5, 4, 3, 2 or 1 amino acid substitutions. Alternatively, each framework region may comprise an amino acid sequence which is at least 90%, 91%, 92%, 93%, 94%, 95%, 96%, 97%, 98% or 99% identical to the amino acid sequences as set forth in the sequence listing.

Preferably, the light chain variable domain comprises the amino acid sequence as set forth as one of SEQ ID NOs: 3, 4, 5, 6, 7 and 8. More preferably, the light chain variable domain comprises the amino acid sequence as set forth as one of SEQ ID NOs: 4, 5, 6, 7 and 8.

Preferably, the heavy chain variable domain comprises the amino acid sequence as set forth as one of SEQ ID NOs: 9, 10, 11, 12, 13 and 14. More preferably, the heavy chain variable domain comprises the amino acid sequence as set forth as one of SEQ ID NOs: 10, 11, 12, 13 and 14.

SEQ ID NOs: 4, 5, 6, 7 and 8 are humanised light chain variable regions. SEQ ID NOs: 10, 11, 12, 13 and 14 are humanised light chain variable regions. The inventors tried all combinations of these light and heavy chain regions resulting in 25 different constructs.

Therefore, in some embodiments, the light chain variable domain comprises the amino acid sequence as set forth as SEQ ID NO: 4 and the heavy chain variable domain comprises the amino acid sequence as set forth as one of SEQ ID NOs: 10, 11, 12, 13 and 14. In a particular embodiment, the light chain variable domain comprises the amino acid sequence as set forth as SEQ ID NO: 4 and the heavy chain variable domain comprises the amino acid sequence as set forth as one of SEQ ID NOs: 10, 12 and 13.

In other embodiments, the light chain variable domain comprises the amino acid sequence as set forth as SEQ ID NO: 5 and the heavy chain variable domain comprises the amino acid sequence as set forth as one of SEQ ID NOs: 10, 11, 12, 13 and 14.

In further embodiments, the light chain variable domain comprises the amino acid sequence as set forth as SEQ ID NO: 6 and the heavy chain variable domain comprises the amino acid sequence as set forth as one of SEQ ID NOs: 10, 11, 12, 13 and 14.

In alternative embodiments, the light chain variable domain comprises the amino acid sequence as set forth as SEQ ID NO: 7 and the heavy chain variable domain comprises the amino acid sequence as set forth as one of SEQ ID NOs: 10, 11, 12, 13 and 14.

In various embodiments, the light chain variable domain comprises the amino acid sequence as set forth as SEQ ID NO: 8 and the heavy chain variable domain comprises the amino acid sequence as set forth as one of SEQ ID NOs: 10, 11, 12, 13 and 14.

Similarly, in some embodiments, the heavy chain variable domain comprises the amino acid sequence as set forth as SEQ ID NO: 10 and the light chain variable domain comprises the amino acid sequence as set forth as one of SEQ ID NOs: 4, 5, 6, 7 and 8.

In other embodiments, the heavy chain variable domain comprises the amino acid sequence as set forth as SEQ ID NO: 11 and the light chain variable domain comprises the amino acid sequence as set forth as one of SEQ ID NOs: 4, 5, 6, 7 and 8.

In further embodiments, the heavy chain variable domain comprises the amino acid sequence as set forth as SEQ ID NO: 12 and the light chain variable domain comprises the amino acid sequence as set forth as one of SEQ ID NOs: 4, 5, 6, 7 and 8.

In alternative embodiments, the heavy chain variable domain comprises the amino acid sequence as set forth as SEQ ID NO: 13 and the light chain variable domain comprises the amino acid sequence as set forth as one of SEQ ID NOs: 4, 5, 6, 7 and 8.

In various embodiments, the heavy chain variable domain comprises the amino acid sequence as set forth as SEQ ID NO: 14 and the light chain variable domain comprises the amino acid sequence as set forth as one of SEQ ID NOs: 4, 5, 6, 7 and 8.

In particular embodiments,
(a) the light chain variable domain comprises the amino acid sequence as set forth as SEQ ID NO: 3 and the heavy chain variable domain comprises the amino acid sequence as set forth as SEQ ID NO: 9;
(b) the light chain variable domain comprises the amino acid sequence as set forth as SEQ ID NO: 4 and the heavy chain variable domain comprises the amino acid sequence as set forth as SEQ ID NO: 10;
(c) the light chain variable domain comprises the amino acid sequence as set forth as SEQ ID NO: 5 and the heavy chain variable domain comprises the amino acid sequence as set forth as SEQ ID NO: 11;
(d) the light chain variable domain comprises the amino acid sequence as set forth as SEQ ID NO: 6 and the heavy chain variable domain comprises the amino acid sequence as set forth as SEQ ID NO: 12;
(e) the light chain variable domain comprises the amino acid sequence as set forth as SEQ ID NO: 7 and the heavy chain variable domain comprises the amino acid sequence as set forth as SEQ ID NO: 13; or
(f) the light chain variable domain comprises the amino acid sequence as set forth as SEQ ID NO: 8 and the heavy chain variable domain comprises the amino acid sequence as set forth as SEQ ID NO: 14.

As indicated below, the sequence of each light chain variable domain and heavy chain variable domain referred to above may differ from the given sequence. For example, the light/heavy chain variable domain may comprise a sequence which is at least 90%, 91%, 92%, 93%, 94%, 95%, 96%, 97%, 98% or 99% identical to the amino acid sequences as set forth in the sequence listing. Alternatively, the light/heavy chain variable domain sequence may differ at up to 10 amino acid positions, although it is preferred that fewer than 10 amino acid substitutions are present so that there may be up to 9, 8, 7, 6, 5, 4, 3, 2 or 1 amino acid substitutions.

As referred to above, in some embodiments, the Light Chain Framework Regions, the Heavy Chain Framework Regions, the Light Chain Variable Domains and the Heavy Chain Variable Domains comprise an amino acid sequence at least 90%, 91%, 92%, 93%, 94%, 95%, 96%, 97%, 98% or 99% identical to the amino acid sequences as set forth above. For example, the Light Chain Framework Regions, the Heavy Chain Framework Regions, the Light Chain Variable Domains and the Heavy Chain Variable Domains may include at most 10, at most 9, at most 8, at most 7, at most 6, at most 5, at most 4, at most 3, at most two or at most one amino acid substitutions in the amino acid sequences as set forth above. Where there is variation in the sequences of the Light Chain Variable Domain and the Heavy Chain Variable Domain, any amino acid substitutions are preferably not in the CDRs. In particular, the Light Chain Framework Regions and/or the Heavy Chain Framework Regions of the antibodies described above may comprise an amino acid sequence at least 90%, 91%, 92%, 93%, 94%, 95%, 96%, 97%, 98% or 99% identical to the amino acid sequences as set forth above. Further, the Light Chain Framework Regions and/or the Heavy Chain Framework Regions may include at most 10, at most 9, at most 8, at most 7, at most 6, at most 5, at most 4, at most 3, at most two or at most one amino acid substitutions in the amino acid sequences as set forth above. Preferably the amino acid substitutions are conservative substitutions as described above. For example, the framework regions may comprise such substitutions in order to humanise the sequence. Preferably, the framework regions are humanised.

In a second embodiment, the antigen binding domain comprises a light chain variable domain and a heavy chain variable domain, wherein the light chain variable domain comprises an LCDR1, an LCDR2 and an LCDR3, wherein LCDR1 comprises the amino acid sequence set forth in SEQ ID NO: 58; LCDR2 comprises the amino acid sequence set forth in SEQ ID NO: 59; and LCDR3 comprises the amino acid sequence set forth in SEQ ID NO: 20; and wherein the heavy chain variable domain comprises an HCDR1, an HCDR2 and an HCDR3, wherein HCDR1 comprises the amino acid sequence set forth in SEQ ID NO: 60; HCDR2 comprises the amino acid sequence set forth in SEQ ID NO: 61; and HCDR3 comprises the amino acid sequence set forth in SEQ ID NO: 62; wherein the sequence of each complementarity determining region may differ from the given sequence at up to two amino acid positions.

As indicated above, the sequence of each CDR may differ from the given sequence at up to two amino acid positions. This means that the CDR may contain one or two amino acid substitutions compared to the given sequence. However, if one or more of the CDRs does contain amino acid substitutions, the antigen binding domain can still selectively bind to ROR1. Preferably, the amino acid substitutions are conservative substitutions.

Preferably, the sequence of each CDR may differ from the given sequence at one amino acid position. This means that the CDR may contain one amino acid substitution compared to the given sequence. Preferably, the amino acid substitution is a conservative substitution. More preferably, the sequence of each CDR does not differ from the given sequence.

Preferably, the light chain variable domain comprises the amino acid sequence as set forth as one of SEQ ID NOs: 3, 4, 5, 6, 7 and 8. More preferably, the light chain variable domain comprises the amino acid sequence as set forth as one of SEQ ID NOs: 4, 5, 6, 7 and 8.

Preferably, the heavy chain variable domain comprises the amino acid sequence as set forth as one of SEQ ID NOs: 9, 10, 11, 12, 13 and 14. More preferably, the heavy chain variable domain comprises the amino acid sequence as set forth as one of SEQ ID NOs: 10, 11, 12, 13 and 14.

As stated above with regard to the first embodiment of the invention, the inventors tried all combinations of the light chain variable domains (SEQ ID NOs: 4, 5, 6, 7 and 8) and heavy chain variable domains (SEQ ID NOs: 10, 11, 12, 13 and 14) resulting in 25 different constructs. Therefore, the description above relating to the combinations of these sequences is also applicable to the second embodiment referred to above.

In particular embodiments, (a) the light chain variable domain comprises the amino acid sequence as set forth as SEQ ID NO: 3 and the heavy chain variable domain comprises the amino acid sequence as set forth as SEQ ID NO: 9;
(b) the light chain variable domain comprises the amino acid sequence as set forth as SEQ ID NO: 4 and the heavy chain variable domain comprises the amino acid sequence as set forth as SEQ ID NO: 10;
(c) the light chain variable domain comprises the amino acid sequence as set forth as SEQ ID NO: 5 and the heavy chain variable domain comprises the amino acid sequence as set forth as SEQ ID NO: 11;
(d) the light chain variable domain comprises the amino acid sequence as set forth as SEQ ID NO: 6 and the heavy chain variable domain comprises the amino acid sequence as set forth as SEQ ID NO: 12;
(e) the light chain variable domain comprises the amino acid sequence as set forth as SEQ ID NO: 7 and the heavy chain variable domain comprises the amino acid sequence as set forth as SEQ ID NO: 13; or
(f) the light chain variable domain comprises the amino acid sequence as set forth as SEQ ID NO: 8 and the heavy chain variable domain comprises the amino acid sequence as set forth as SEQ ID NO: 14.

The sequence of each light chain variable domain and heavy chain variable domain referred to above may differ from the given sequence. For example, the light/heavy chain variable domain may comprise a sequence which is at least 90%, 91%, 92%, 93%, 94%, 95%, 96%, 97%, 98% or 99% identical to the amino acid sequences as set forth in the sequence listing. Alternatively, the light/heavy chain variable domain sequence may differ at up to 10 amino acid positions, although it is preferred that fewer than 10 amino acid substitutions are present so that there may be up to 9, 8, 7, 6, 5, 4, 3, 2 or 1 amino acid substitutions.

For all the embodiments described above, one skilled in the art will be aware that any substitutions will retain critical amino acid residues necessary for correct folding and stabilizing between the $V_H$ and the $V_L$ regions, and will retain the charge characteristics of the residues in order to preserve the low pI and low toxicity of the CARs. Thus, one of skill in the art can readily review the sequences shown above, identify a conservative substitution, and produce the conservative variant using well-known molecular techniques.

Epitope mapping has been carried out for the antigen binding domains discussed above. In one embodiment, it has been found that residue Gln-261 of human ROR1 is essential for the antigen binding domain. Therefore, there is also provided an antigen binding domain that binds to an epitope of ROR1, wherein the epitope comprises amino acid Gln-261.

The antigen binding domain may have the structure of an antibody fragment such as Fab, F(ab')$_2$, and Fv which include a heavy chain and light chain variable region and are capable of binding the epitopic determinant on ROR1. These antibody fragments retain the ability to selectively bind with the antigen and are described above. Methods of making these fragments are known in the art (see for example, Harlow and Lane, *Antibodies: A Laboratory Manual*, Cold Spring Harbor Laboratory, New York, 1988).

In a further group of embodiments, the antigen binding domain may have the structure of an Fv antibody, which are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra). Dimers of a single chain antibody (scFV$_2$), are also contemplated.

Antibody fragments comprising the antigen binding domain can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

The antigen binding domains, antibodies or antibody fragments disclosed herein can be derivatized or linked to another molecule (such as another peptide or protein). In general, the antibody or portion thereof is derivatized such that the binding to the ROR1 polypeptide is not affected adversely by the derivatization or labelling. For example, the antibody can be functionally linked, for example, by chemical coupling, genetic fusion, noncovalent association or otherwise to one or more other molecular entities, such as another antibody (for example, a bispecific antibody or a diabody), a detection agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company (Rockford, Ill.).

An antigen binding domain that specifically binds a ROR1 polypeptide can be labelled with a detectable moiety or marker as described above.

An antigen binding domain can also be labelled with a radiolabeled amino acid. Examples of radiolabels include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$. The radiolabel may be used for both diagnostic and therapeutic purposes.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

An antigen binding domain can also be derivatized with a chemical group such as polyethylene glycol (PEG), a methyl or ethyl group, or a carbohydrate group. These groups may be useful to improve the biological characteristics of the antigen binding domain, such as to increase serum half-life or to increase tissue binding.

Polynucleotides and Expression

Nucleotide sequences encoding an antigen binding domain that specifically binds a ROR1 polypeptide are also provided. Expression vectors are also provided for their efficient expression in cells (for example, T cells).

Recombinant expression of an antigen binding domain generally requires construction of an expression vector containing a polynucleotide that encodes the antibody or antibody fragment. Replicable vectors are provided including a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of an antibody molecule (see, e.g., U.S. Pat. Nos. 5,981,216; 5,591,639; 5,658,759 and 5,122,464) and the variable domain of the antibody may be cloned into such a vector for expression of the entire heavy, the entire light chain, or both the entire heavy and light chains.

Nucleic acid molecules (also referred to as polynucleotides) encoding the polypeptides provided herein (including, but not limited to antigen binding domains) can readily be produced by one of skill in the art. For example, these nucleic acids can be produced using the amino acid sequences provided herein (such as the CDR sequences, heavy chain and light chain sequences), sequences available in the art (such as framework sequences), and the genetic code.

One of skill in the art can readily use the genetic code to construct a variety of functionally equivalent nucleic acids, such as nucleic acids which differ in sequence but which encode the same antibody sequence, or encode a conjugate or fusion protein including the $V_L$ and/or $V_H$ nucleic acid sequence.

Nucleic acid sequences encoding the antigen binding domains that specifically bind a ROR1 polypeptide, can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

Any of the nucleic acids encoding any of the antigen binding domains, $V_H$ and/or $V_L$, disclosed herein (or fragment thereof) can be expressed in a recombinantly engineered cell such as bacteria, plant, yeast, insect and mammalian cells. These antibodies can be expressed as individual $V_H$ and/or $V_L$ chain, or can be expressed as a fusion protein. An immunoadhesin can also be expressed. Thus, in some examples, nucleic acids encoding a $V_H$ and $V_L$, and immunoadhesin are provided. The nucleic acid sequences can optionally encode a leader sequence.

To create a single chain antibody, (scFv) the $V_H$- and $V_L$-encoding DNA fragments are operatively linked to another fragment encoding a flexible linker, e.g., encoding the amino acid sequence $(Gly_4$-$Ser)_3$, such that the $V_H$ and $V_L$ sequences can be expressed as a contiguous single-chain protein, with the $V_L$ and $V_H$ domains joined by the flexible linker (see, e.g., Bird et al., Science 242:423-426, 1988; Huston et al., Proc. Natl. Acad. Sci. USA 85:5879-5883, 1988; McCafferty et al., Nature 348:552-554, 1990). Optionally, a cleavage site can be included in a linker, such as a furin cleavage site.

The nucleic acid encoding the $V_H$ and/or the $V_L$ optionally can encode an Fc domain (immunoadhesin). The Fc domain can be an IgA, IgM or IgG Fc domain. The Fc domain can be an optimized Fc domain, as described in U.S. Published Patent Application No. 20100/093979, incorporated herein by reference. In one example, the immunoadhesin is an IgG$_1$ Fc.

It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines. Once the expression vector is transferred to a host cell by conventional techniques, the transfected cells are then cultured by conventional techniques, such as to produce an antibody. Thus, host cells are provided containing a polynucleotide encoding an antigen binding domain, or a heavy or light chain thereof, or portion thereof, operably linked to a heterologous promoter. In certain embodiments for the expression of double-chained antigen binding domains, vectors encoding both the heavy and light chains may be co-expressed in the host cell for expression of the entire immunoglobulin molecule, as detailed below.

Mammalian cell lines available as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), SP20, CRL7O3O and HsS78Bst cells. In one embodiment, human cell lines are of use. In one embodiment, the human cell line PER.C6. (Crucell, Netherlands) can be used. Additional cell lines which may be used as hosts for expression of recombinant antibodies include, but are not limited to, insect cells (e.g. Sf21/Sf9, Trichoplusia ni Bti-Tn5b1-4) or yeast cells (e.g. *S. cerevisiae*, Pichia, U.S. Pat. No. 7,326,681), plant cells (US Published Patent Application No. 20080066200); and chicken cells (PCT Publication No. WO2008142124).

The host cell can be a gram positive bacteria including, but not limited to, *Bacillus, Streptococcus, Streptomyces, Staphylococcus, Enterococcus, Lactobacillus, Lactococcus, Clostridium, Geobacillus*, and *Oceanobacillus*. Methods for expressing protein in gram positive bacteria, such as *Lactobacillus* are well known in the art, see for example, U.S. Published Patent Application No. 20100/080774. Expression vectors for *Lactobacillus* are described, for example in U.S. Pat. Nos. 6,100,388, and 5,728,571. Leader sequences can be included for expression in *Lactobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

One or more DNA sequences encoding the antigen binding domain or fragment thereof can be expressed in vitro by DNA transfer into a suitable host cell. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

The expression of nucleic acids encoding the isolated proteins described herein can be achieved by operably linking the DNA to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used.

Eukaryotic cells can also be cotransformed with polynucleotide sequences encoding the antigen binding domain, labeled antigen binding domain, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antigen binding domains of the present disclosure can also be constructed in whole or in part using standard peptide synthesis well known in the art.

Once expressed, the recombinant immunoconjugates, antigen binding domain, and/or effector molecules can be purified according to standard procedures of the art, including ammonium sulfate precipitation, affinity columns, column chromatography, and the like (see, generally, R. Scopes, PROTEIN PURIFICATION, Springer-Verlag, N.Y., 1982). The antigen binding domains, immunoconjugates and effector molecules need not be 100% pure. Once purified, partially or to homogeneity as desired, if to be used therapeutically, the polypeptides should be substantially free of endotoxin.

Methods for expression of antibodies and/or refolding to an appropriate active form, including single chain antibodies, from bacteria such as *E. coli* have been described and are well-known and are applicable to the antigen binding domains disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989.

Compositions and Therapeutic Methods

Cells comprising the antigen binding domains discussed above for use in the treatment of cancer in a subject wherein the cell comprising the ROR1 selective CAR is administered to the subject to cause selective depletion of malignant cells are also disclosed as well as methods for treating cancer in a subject comprising administering to a subject a cell comprising the antigen binding domains discussed above to cause selective depletion of malignant cells.

Preferably, the cancer is leukaemia (such as Chronic Lymphocytic Leukaemia (CLL), Acute Lymphoblastic Leukaemia (ALL), Mantle Cell Leukaemia or Hairy Cell Leukaemia), pancreatic cancer, prostate cancer, colon cancer, bladder cancer, ovarian cancer, glioblastoma, testicular cancer, uterine cancer, adrenal cancer, breast cancer, lung cancer, melanoma, neuroblastoma, sarcoma, renal cancer. Furthermore, ROR1 is expressed on a subset of cancer stem cells.

The cancer or tumour does not need to be completely eliminated for the CAR T cells to be effective. For example, the CAR T cells can reduce the tumour by a desired amount, for example by at least 10%, at least 20%, at least 50%, at least 60%, at least 70%, at least 80%, at least 90%, at least 95%, at least 98%, or 100%, as compared to the absence of the composition.

Administration of the CART cells of the present invention may result in a 5, 10, 20, 50, 75, 90, 95 or 99% depletion, i.e. reduction in malignant cells.

In another example, the subject can also be administered an effective amount of an additional agent, such as a chemotherapy agent. The methods can include administration of one or more additional agents known in the art. The agent may be conjugated to the CAR T cell. The agent may be a chemotherapeutic entity. The chemotherapeutic entity may be a cytotoxic drug. A chemotherapeutic agent contemplated includes, without limitation, alkylating agents, nitrosoureas, ethylenimines/methylmelamine, alkyl sulfonates, antimetabolites, pyrimidine analogs, epipodophylotoxins, enzymes such as L-asparaginase; biological response modifiers such as IFNa, IL-2, G-CSF and GM-CSF; platinium coordination complexes such as cisplatin and carboplatin, anthracenediones, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropinreleasing hormone analogs and leuprolide; and non-steroidal antiandrogens such as flutamide.

A therapeutically effective amount of a ROR1-specific CART cell will depend upon the severity of the disease and the general state of the patient's health. A therapeutically effective amount of the CAR T cells can provide either subjective relief of a symptom(s) or an objectively identifiable improvement as noted by the clinician or other qualified observer. As noted above, these compositions can be administered in conjunction with another therapeutic agent, either simultaneously or sequentially. For any application, the CAR T cells can be combined with chemotherapy.

Single or multiple administrations of the compositions including the CAR T cells, that are disclosed herein, are administered depending on the dosage and frequency as required and tolerated by the patient. In any event, the composition should provide a sufficient quantity of at least one of the antibodies disclosed herein to effectively treat the patient. The dosage can be administered once but may be applied periodically until either a therapeutic result is achieved or until side effects warrant discontinuation of therapy. In one example, a dose of the CAR T cells is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Compositions are further disclosed that include the CAR T cells in a carrier. The compositions can be prepared in unit dosage forms for administration to a subject. The amount and timing of administration are at the discretion of the treating physician to achieve the desired purposes. The antibody and/or nucleic acid can be formulated for systemic or local administration. In one example, the CAR T cells are formulated for parenteral administration, such as intravenous administration. In some embodiments, administration is intramuscular.

Active ingredients can also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). Specifically, liposomes containing the immunogens or antibodies can be prepared by such methods as described in Epstein et al., Proc. Natl. Acad. Sci. USA, 82:3688 (1985); Hwang et al., Proc. Natl. Acad. Sci. USA, 77:4030 (1980); and U.S. Pat. Nos. 4,485,045 and 4,544,545. Liposomes with enhanced circulation time are disclosed in U.S. Pat. No. 5,013,556. The everse-phase evaporation method can be used with a lipid composition comprising phosphatidylcholine, cholesterol and PEG-derivatized phosphatidylethanolamine (PEG-PE). Liposomes are extruded through filters of defined pore size to yield liposomes with the desired diameter. Polypeptides of the present invention can be conjugated to the liposomes as described, for example, in Martin et al., J. Biol. Chem., 257:286-288 (1982) via a disulfide interchange reaction.

The compositions for administration can include a solution of the CAR T Cells, dissolved in a pharmaceutically acceptable carrier, such as an aqueous carrier. A variety of aqueous carriers can be used, for example, buffered saline and the like. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of CAR T Cells in these formulations can vary widely, and will be selected primarily based on fluid volumes, viscosities, body weight and the like in accordance with the particular mode of administration selected and the subject's needs. In some embodiments, administration is intravenous.

Controlled-release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the CAR T Cells disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)).

A typical pharmaceutical composition for intravenous administration includes about $1\times10^6$ to $1\times10^8$ T cells/kg. Alternatively, this may be about $1\times10^6$ to $1\times10^8$ T cells/m². Actual methods for preparing administrable compositions will be known or apparent to those skilled in the art and are described in more detail in such publications as *Remington's Pharmaceutical Science*, 19th ed., Mack Publishing Company, Easton, Pa. (1995).

The following examples are provided to illustrate certain particular features and/or embodiments. These examples should not be construed to limit the disclosure to the particular features or embodiments described. The examples should be read in combination with the figures which are as follows:

FIG. 1: a diagram of the αβ T-cell Receptor/CD3 Complex. The T-cell receptor is formed from 6 different protein chains which must assemble in the endoplasmic reticulum to be expressed on the cell surface. The four proteins of the CD3 complex (CD3ζ, CD3γ, CD3ε and CD3δ) sheath the T-cell Receptor (TCR), This TCR imbues the complex with specificity of a particular antigen and is composed of two chains: TCRα and TCRβ. Each TCR chain has a variable component distal to the membrane and a constant component proximal to the membrane.

Figure 2:
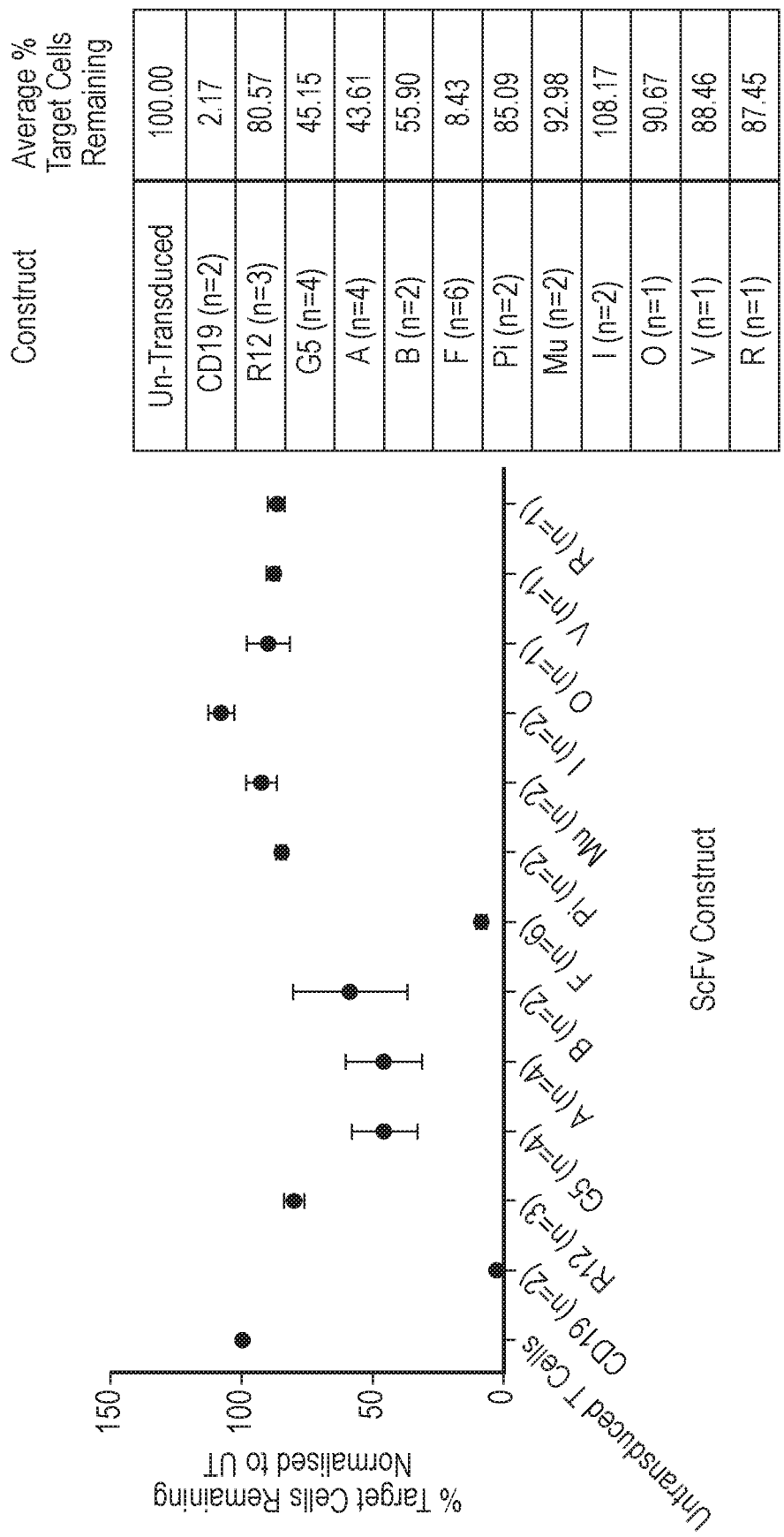

FIG. 2: Healthy donor T-cells were transduced to express 2nd generation CAR (with 41BB and CD3zeta intracellular signalling domains) with 10 novel ScFv binders generated by the inventors (referred to as clones G5, A, B, F, Pi, Mu, I, O, V and R) and the published R12 ScFv and CD19fmc63 ScFv. They were cultured with SKW6.4 cells at a 2:1 Effector:Target. Number of live target cells at 24 hours was assessed by a FACS based killing assay and normalized to live cells remaining with un-transduced T-cells. (Number of individual donors tested). Error bars represent Standard Error of the Mean.

Figure 3:
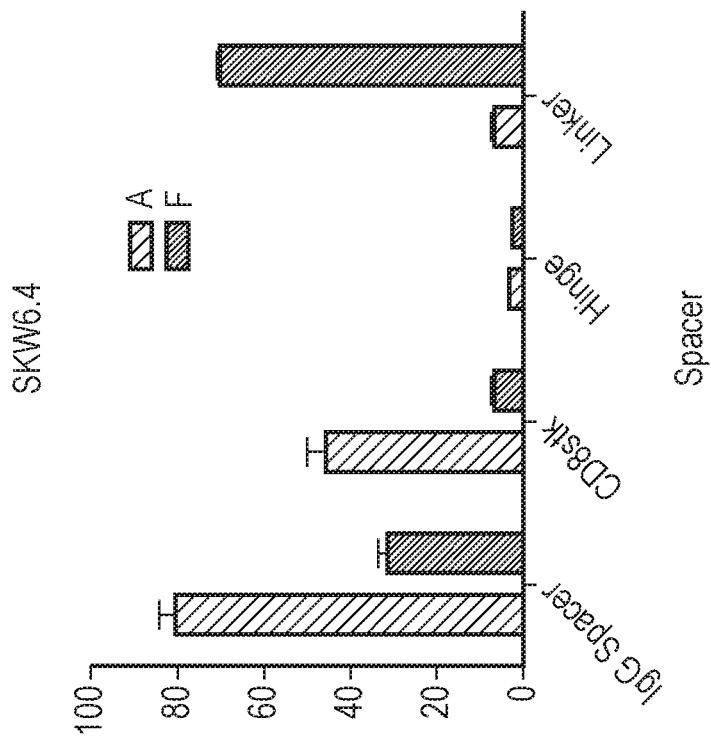
Figure 3:
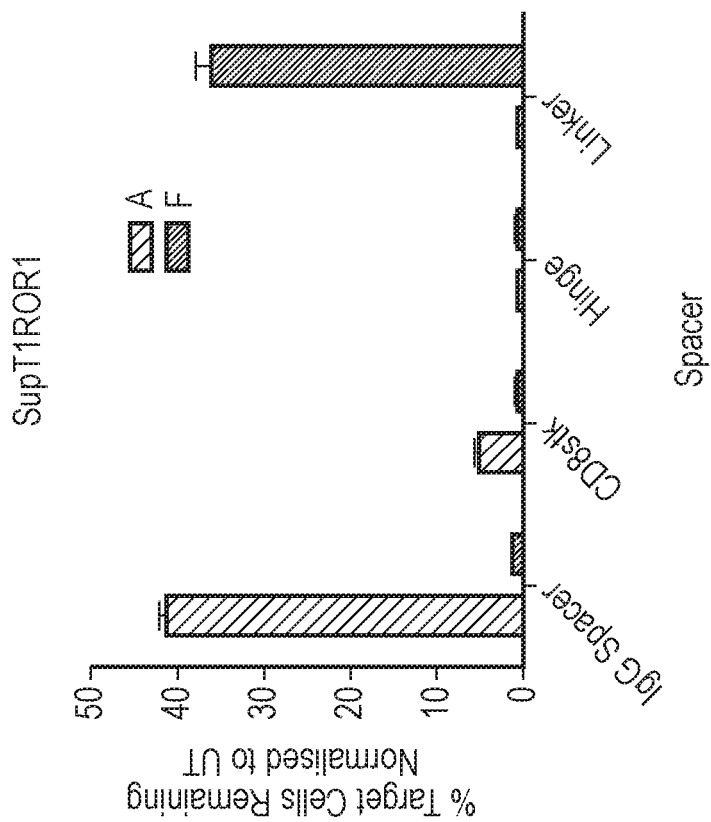

FIG. 3: Healthy donor T-Cells were transduced with CAR constructs for both Clone A and F which differed by the extracellular spacer domain. Clone A showed optimal cytotoxicity with shorter spacers such as hinge and linker, whilst clone F showed better toxicity with those of moderate length such as the CD8 stalk and Hinge.

Figure 4:
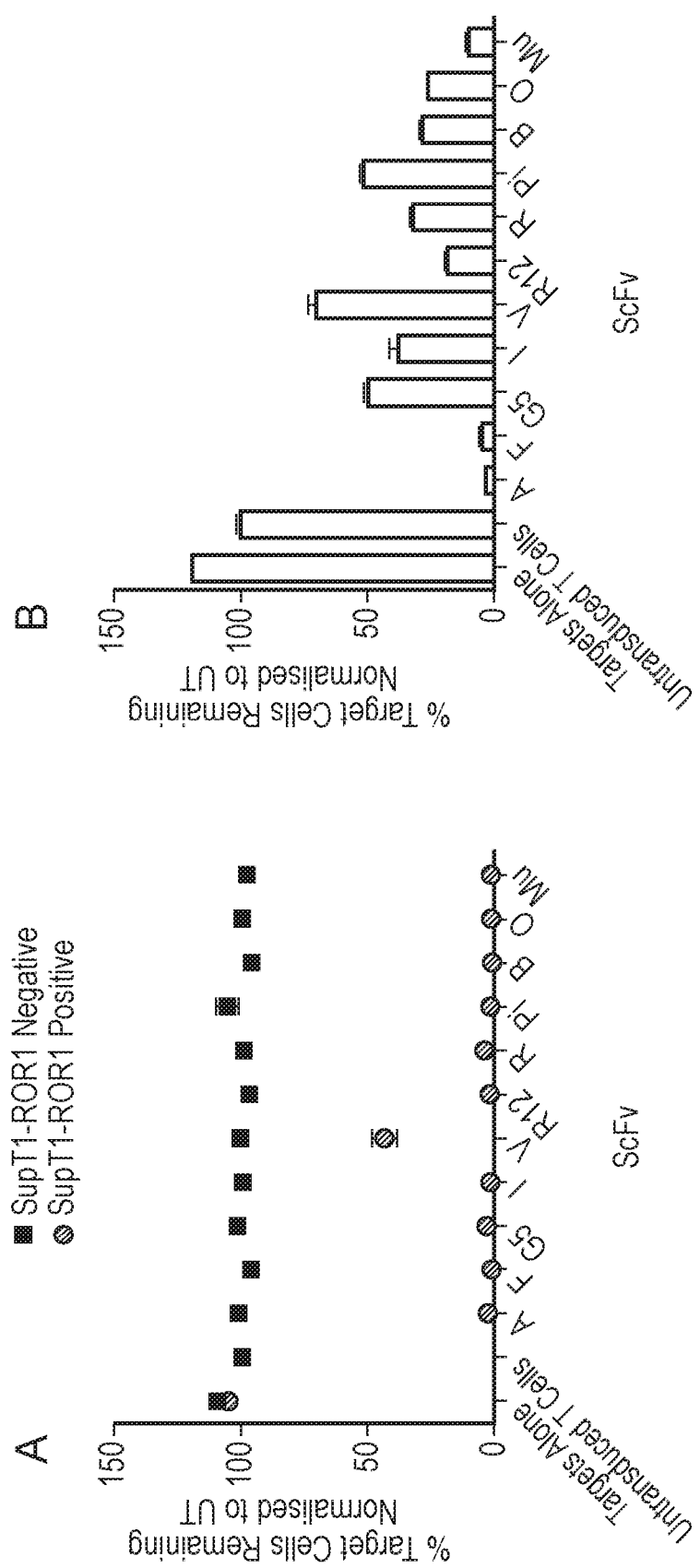

FIG. 4: The CD8a spacer was substituted for the hinge spacer for all of the above ScFv based CAR constructs and T-cells from a single healthy donor were transduced to express the CAR. T-cells were co-cultured with SupT1-ROR1 negative and SupT1-ROR1 positive cell lines (A), which showed that with the exception of Clone V, all clones resulted in near total elimination of SupT1-ROR1 targets. When assessed on SKW6.4 cells all constructs showed improved cytotoxicity compared to previous CD8 spacer constructs. Target and Effector cells were plated at a 1:1 ratio.

Figure 5:
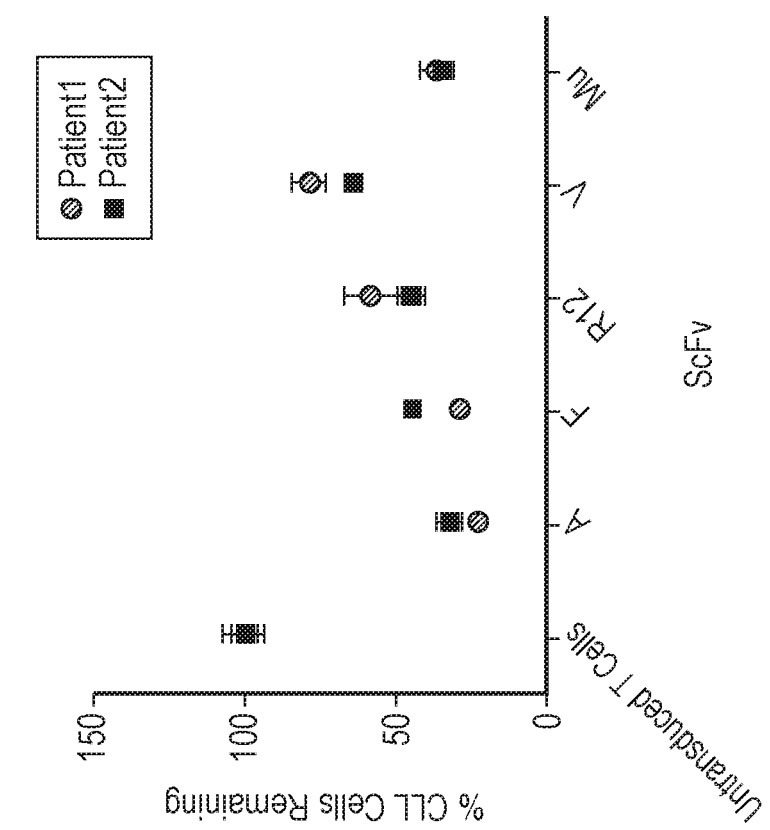
Figure 5:
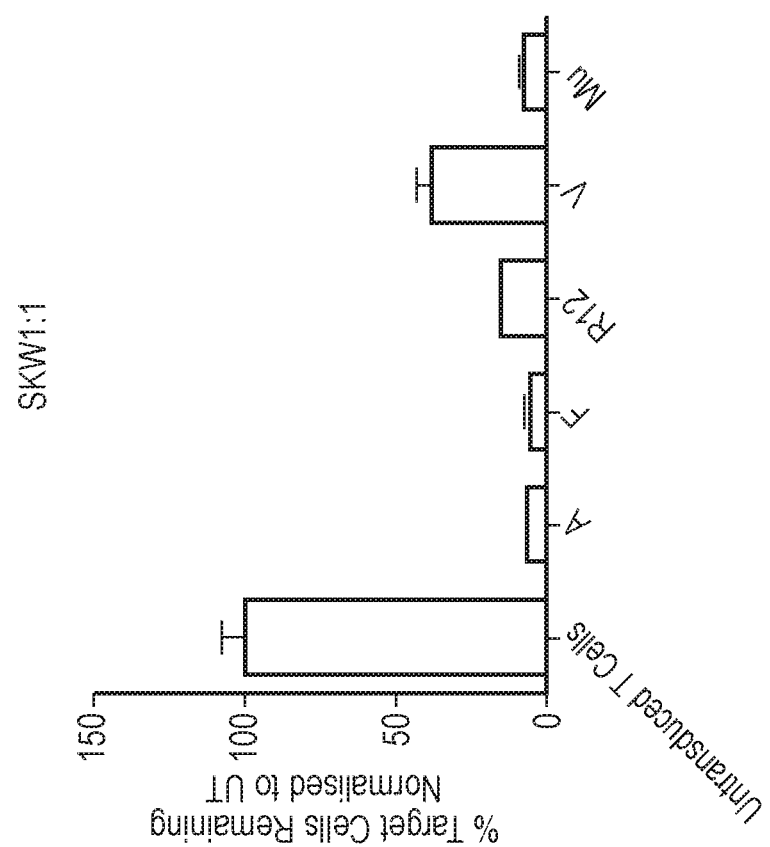

FIG. 5: At 1:1 Effector:Target ratio in a FACS based killing assay Clones A and F showed superior killing against R12, V and Mu against SKW6.4 cell lines. The difference in cytotoxicity were less when the same T-cells targeted primary CLL cells expressing ROR1 but cytotoxicity was still seen.

Figure 6:
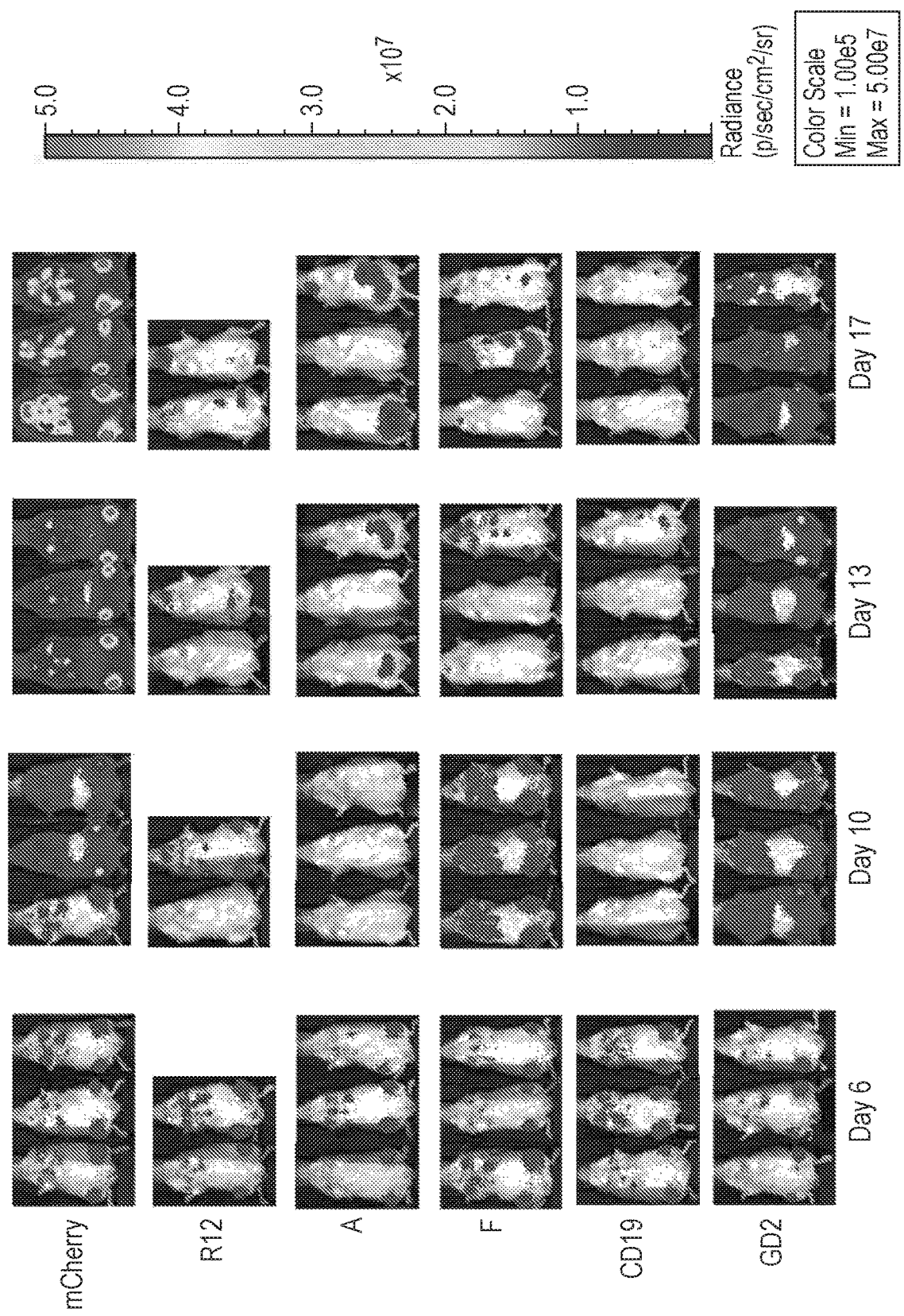

FIG. 6: In vivo function of the newly developed ScFv sequences in CAR format in a murine model utilising Jekol cells transduced to express firefly luciferase. Mice were injected with 0.5×10⁶ Jekol cells and 5 days later were injected with 4×10⁶ CAR T-cells via tail vein. Bioluminescent imaging was undertaken with D-Luciferin at appropriate time points.

Figure 7:
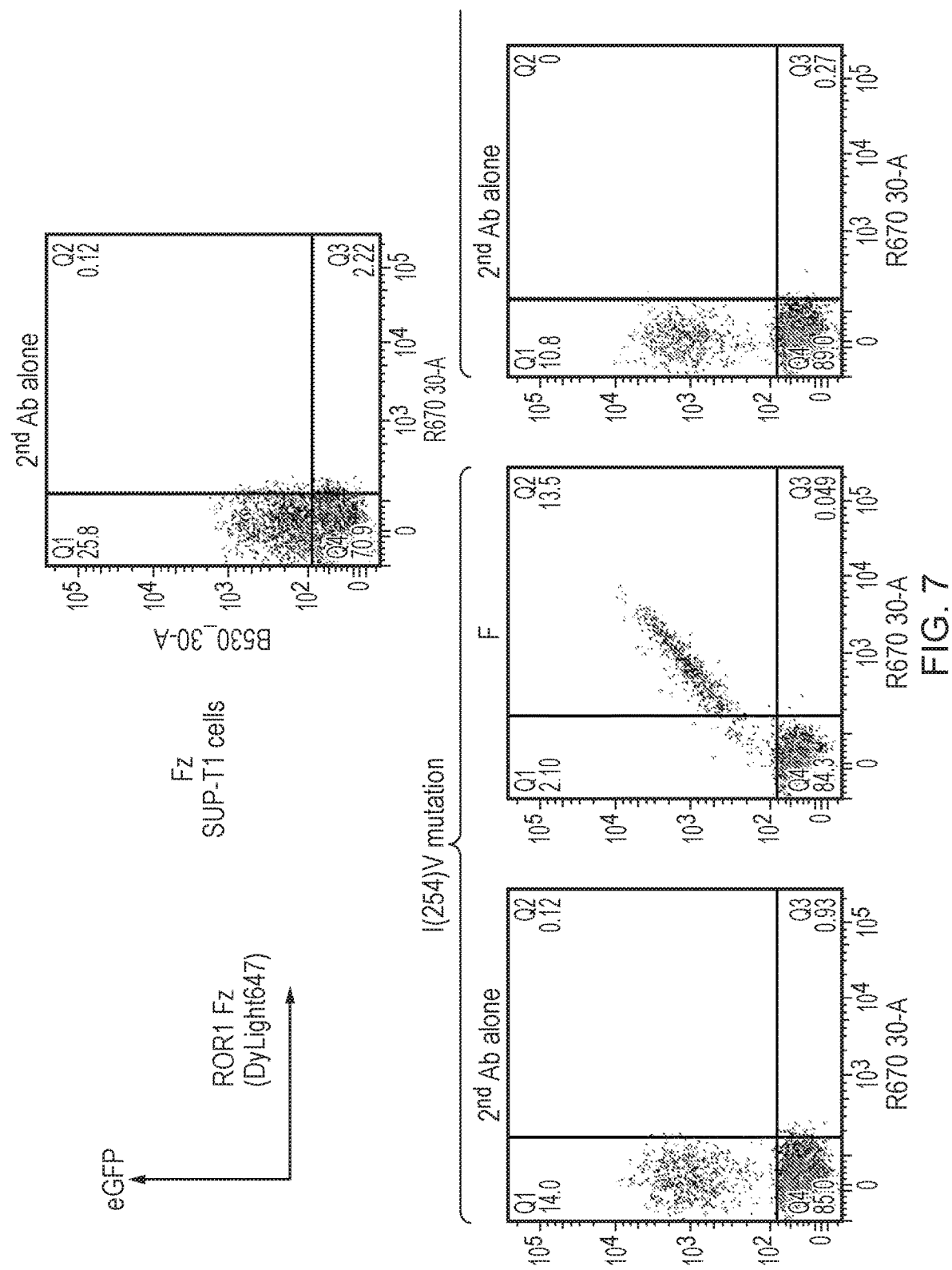
Figure 7:
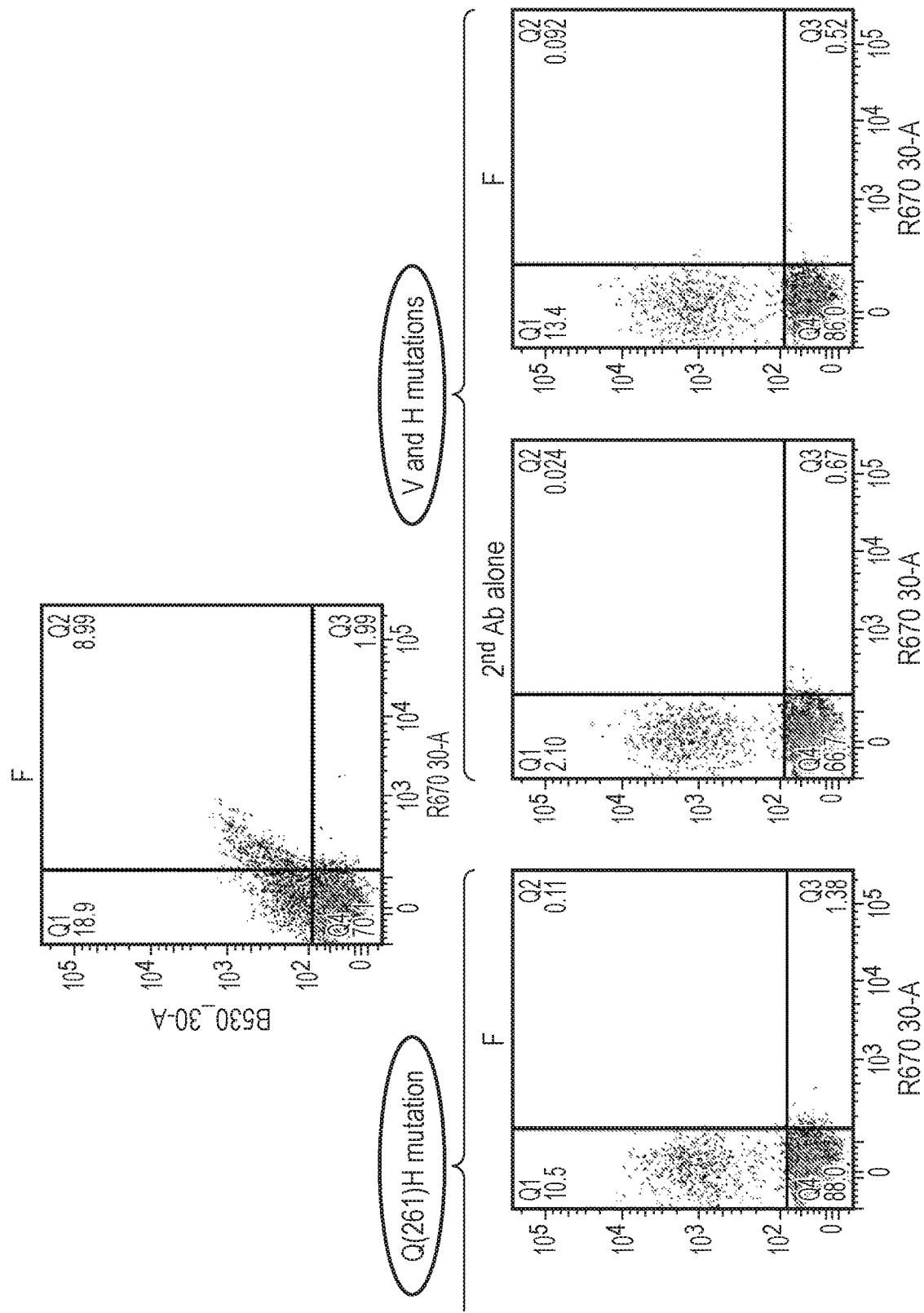

FIG. 7: Point mutations were generated for the Fz domain of human ROR1 at positions 254 and 261. The particular mutations used were I(254)V and Q(261)H. It was found that the Q(261)H substitution reduced or stopped the clone F antibody binding to ROR1-Fz domain, whereas the I(254)V substitution did not seem to affect binding. Further, the combination of Q(261)H and I(254)V also prevented antibody binding.

Figure 8:
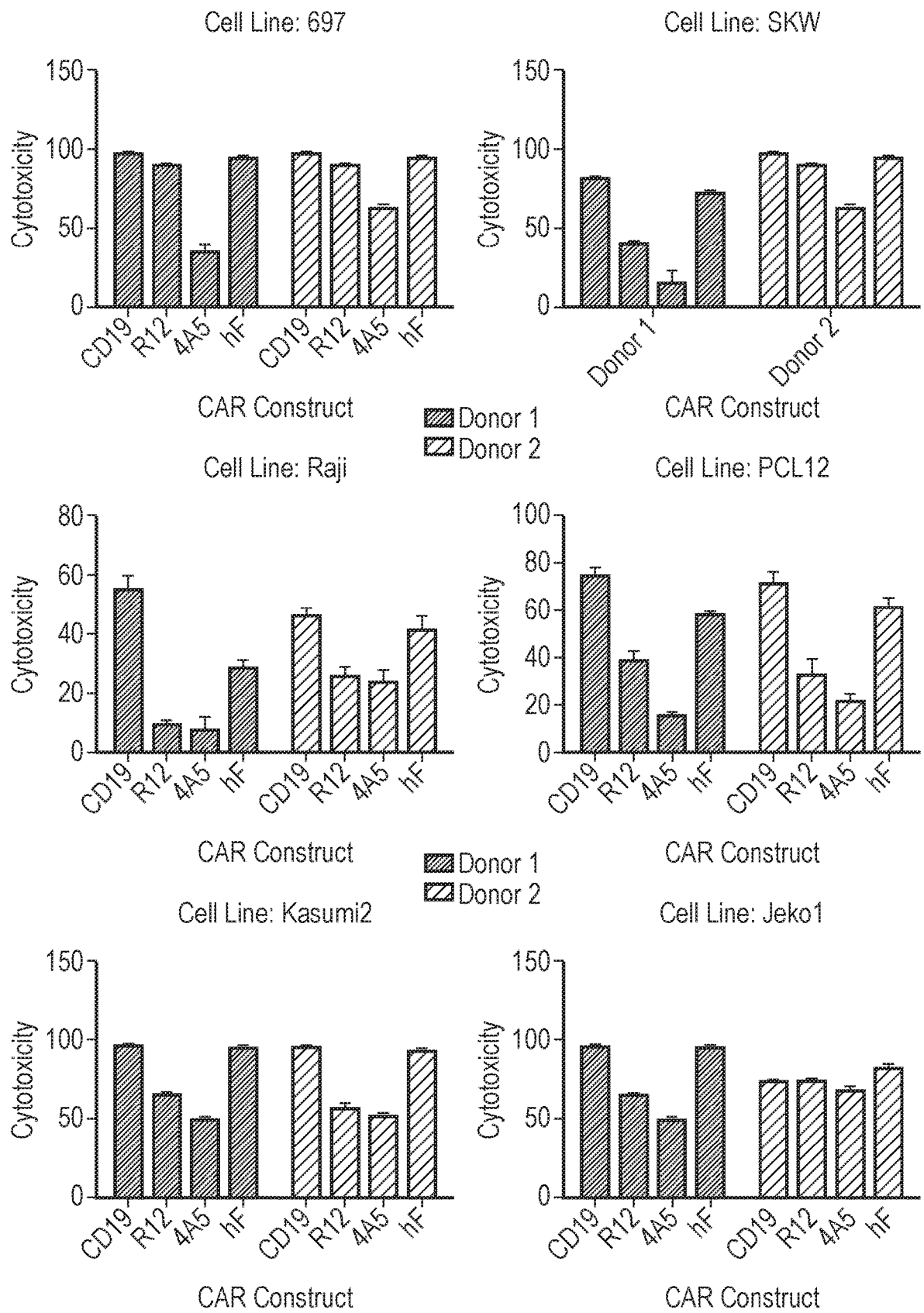

FIG. 8: Cytotoxicity of humanised clone F ROR1-CAR T-cells (hF) against a panel of ROR1 positive cell lines which constitutively express ROR1 representative of ALL (697, Kasumi2), Lymphoma (Jekol, Raji) and CLL (SKW, PCL12) compared to ROR1 ScFvs CD19, R12 and 4A5.

Figure 9:
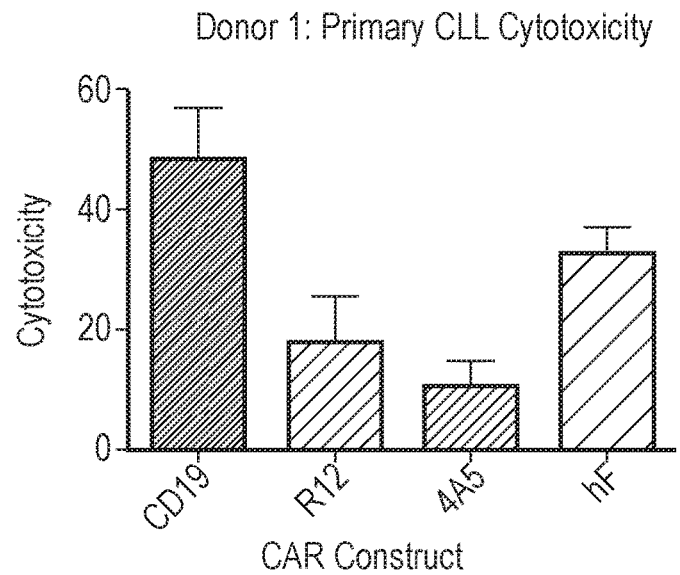

FIG. 9: Cytotoxicity of hF, CD19fmc63, R12 and 4A5 ROR1 CAR T-cells co-cultured with primary CLL cells which had been CFSE labelled and isolated using a B-CLL isolation kit (Miltenyi Bioscience) in a 4:1 Effector:Target ratio.

Figure 10:
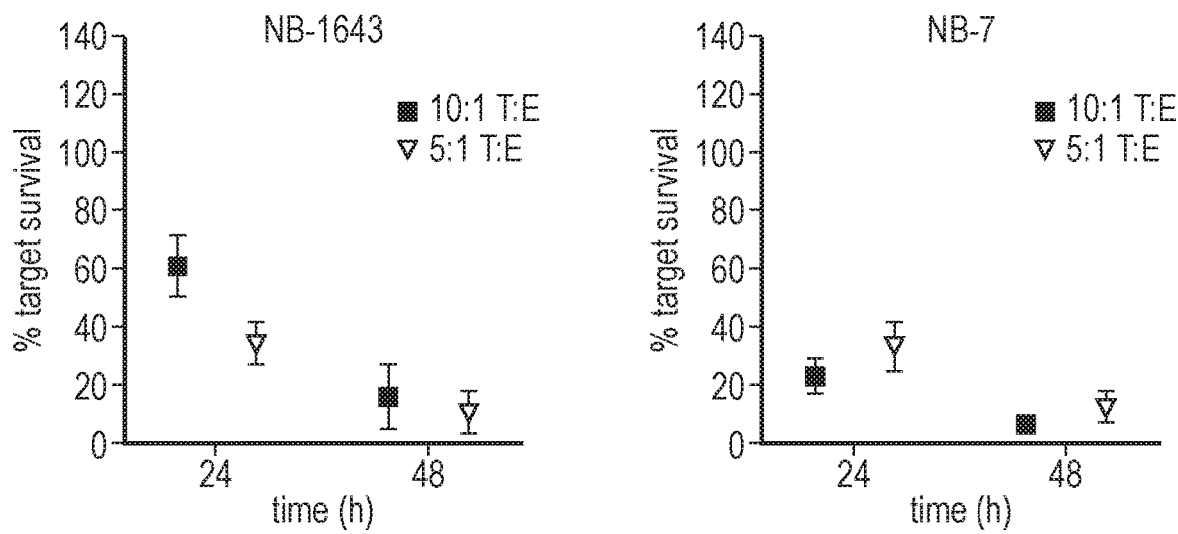
Figure 10:
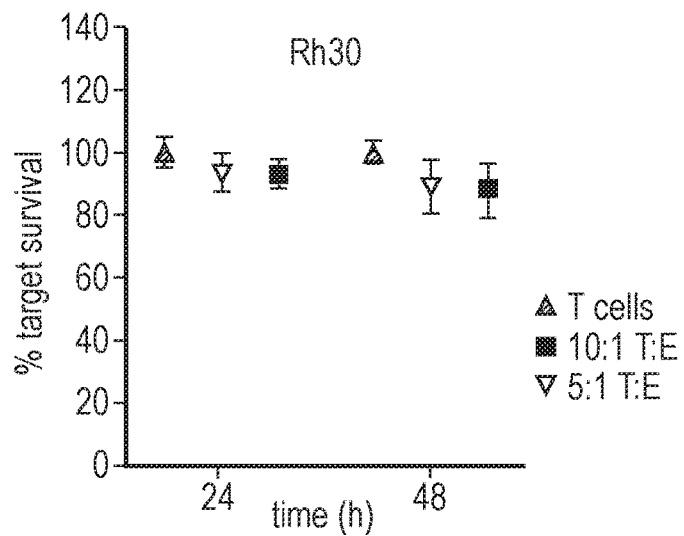

FIG. 10: Cytotoxicity against ROR1 positive neuroblastoma cell lines.

Figure 11:
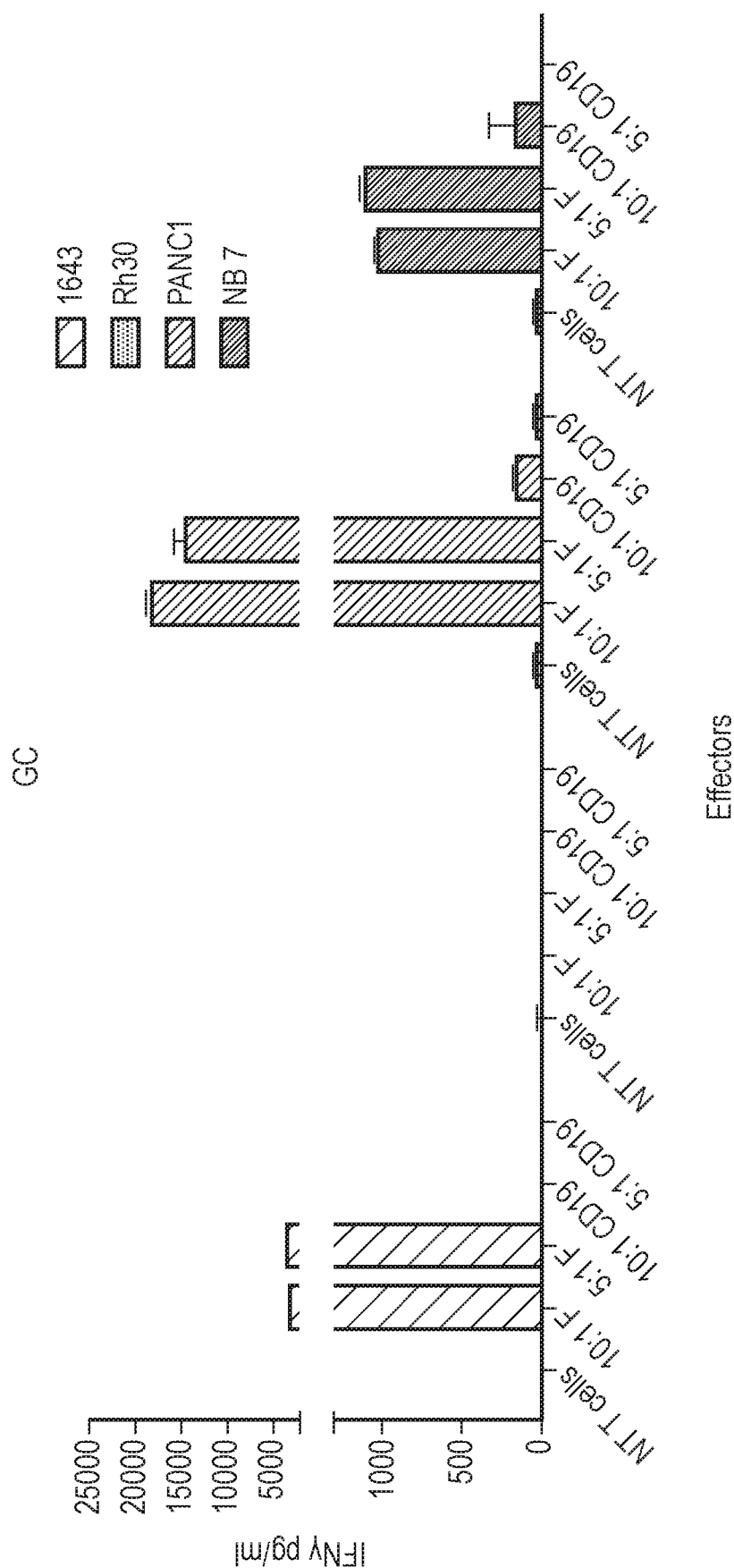
Figure 11:
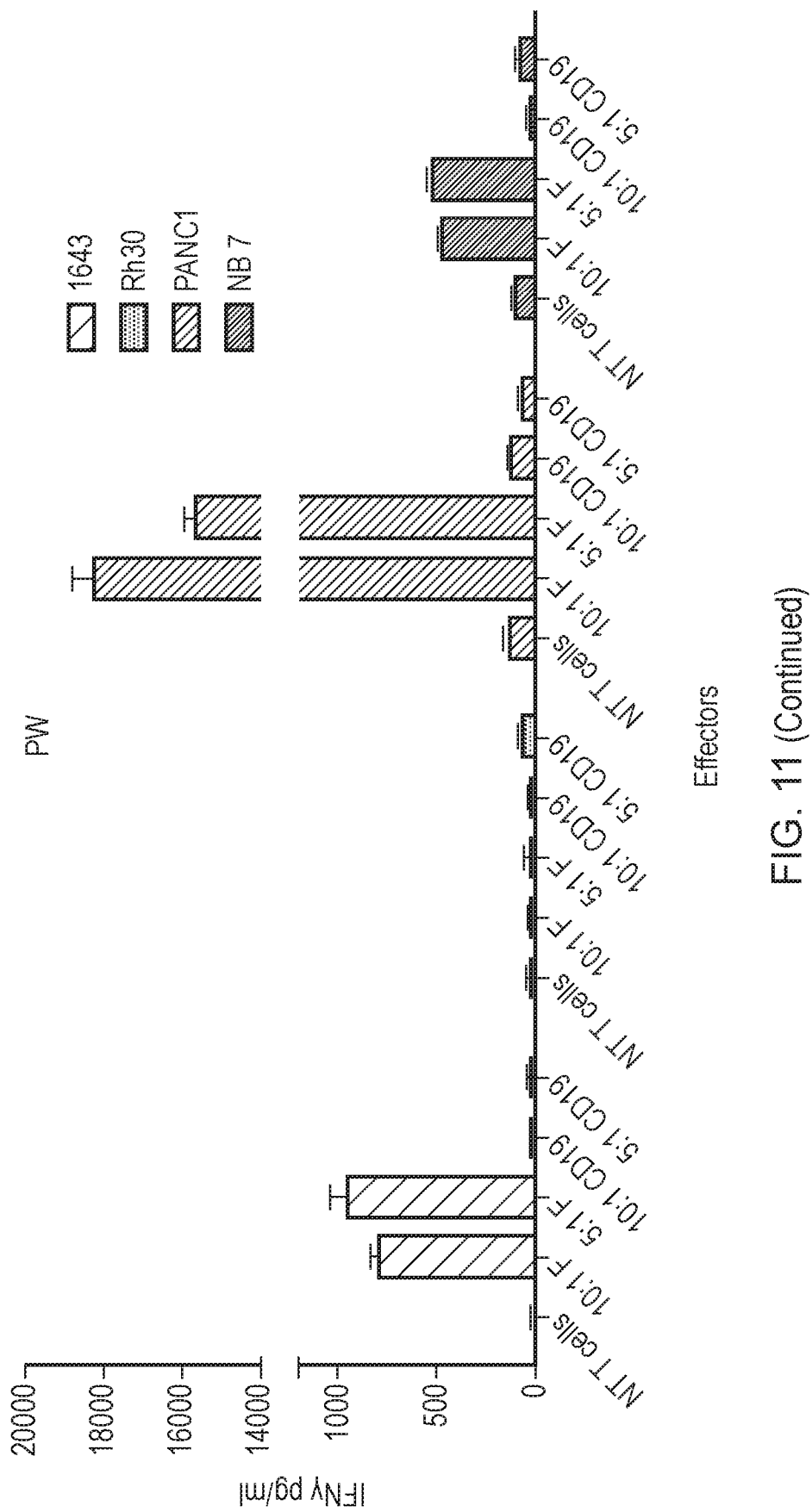

FIG. 11: Clone F ROR1 CAR T cells lead to significant IFNg secretion compared to CD19 CAR T cells against ROR1 positive (1643, PANC1 and NB-7) cell lines.

EXAMPLES

Example 1

Materials and Methods
Molecular Biology

DNA cloning was undertaken using standard laboratory protocols. Restriction enzymes, Phusion Taq polymerase, Quickligase and DH5a competent cells were obtained from New England Biolabs. DNA was run on 1-2% TBE Agarose Gels depending on the expected band size and stained with either Ethidium Bromide (Sigma-Aldrich), SybrSafe Gel Stain (Life Technologies) or Gelstar (Lonza). Gel extraction and PCR clean-up was undertaken with SV Wizard Gel and Purification Kit (Promega).

Bacteria were grown in Lennox Broth or Terrific Broth (Fisher Scientific); Minipreps, Midipreps and Megapreps plasmid purification kits were from Mancherey Nagel whilst Maxipreps used Qiagen kits as per the manufacturer's instructions. DNA concentration was assessed with a Nanodrop (Thermo Scientific) and sequencing was performed through Source Bioscience or Beckman Coulter Genomics. Oligonucleotide primers and G-Block oligonucleotides were obtained from Integrated DNA Technologies and Gene Synthesis was undertaken by Genscript.

Tissue Culture

Dulbecco's Modified Eagle's Medium (DMEM), Iscove's Modified Dulbecco's Medium (IMDM) and Roswell Park Memorial Institute (RPMI) along with Foetal Calf Serum (FCS) was obtained from Gibco, Life Technologies. DMEM, IMDM and RPMI were all supplemented with 10% FCS and Glutamax and RPMI was supplemented with HEPES. No antibiotics were used in routine culture but flow sorting utilised Normocin (Invivogen).

Nalm-6, SupT1, K562 and SKW6.4 cells have been long established in the laboratory and all were grown in RPMI with 10% FCS. HEK293T cells were thawed from master stocks and grown in IMDM and 10% FCS.

Antigen Binding Capacity Measurements

Qifikit beads were used to assess the number of target antigens per cell using the manufacturer's instructions (Dako, Agilent Technologies). In brief, the cells of interest were incubated with the same concentration of unconjugated murine anti-human ROR1 or CD19 antibodies, washed twice with PBS and then stained with anti-murine FC conjugated antibody linked to FITC or APC. Calibrated beads with known numbers of binding sites were stained in the same way allowing the construction of a standard curve with mean fluorescence intensity measurements relating to absolute antigens per cell.

Lentiviral Production

Second generation lentivirus was produced using standard laboratory protocols. Briefly, 1.7×10⁶ HEK293T cells were plated in 10 cm dishes on day 1 followed by transfection with GeneJuice reagent (Merck Millipore) combined with transfer vector, packaging vector pCMVdR8.74 and VSVG pseudo-typed envelope vector pMD.G2 on day 3. Supernatant was harvested on day 5 and centrifuged for 5 minutes at 800 G to remove contaminating cellular material and filtered through 0.2 micron PES filters (Merck Millipore) before being used directly for transduction or being frozen and stored at −80° C. for subsequent use. Third generation lentiviral vectors were produced using pMDLg/RRE, pMDG2 and pRSV/Rev plasmids.

T Cell Transduction

Healthy volunteer peripheral blood was collected with EDTA anticoagulation and Peripheral Blood Mononuclear Cells (PBMC) isolated by Ficoll-Paque Plus (GE Healthcare) centrifugation. PBMCs were re-suspended at 2×10⁶/ml and seeded at 1 ml per 24 well plate and activated with MACS GMP CD3 and CD28 antibodies at 0.5 mg/ml (Miltenyi Biotec) or CD3/28 beads (Invitrogen). The next day fresh R10 was added with IL-2 to a final concentration of 100 IU/ml (if antibody activated) and 6 hours later cells were harvested, counted and re-suspended at 0.6×10⁶/ml and 0.5 ml was seeded into a 24 well plate coated with Retronectin (Takara Bio). 1.5 ml of lentiviral supernatant was added to each well and spun for 40 minutes at 1000 G. Two days later cells were harvested, re-suspended at 0.5×10⁶/ml and left to expand for a further two days before being used for co-culture and FACS experiments. Natural Killer cells were removed via CD56 bead depletion (Miltenyi Biotec)

Truncated ROR1 Cell Lines

The complete extracellular domain of ROR1 was synthesised and PCR amplification of the various domains (Immunoglobulin, Frizzled and Kringle) was undertaken. These primers, as well as the complete extracellular domain, had compatible ends and were inserted into the SFG transfer plasmid and transduced into SupT1 cells. The extracellular domains were tethered to the membrane with a transmembrane domain fused to eGFP.

Flow Cytometry

Antibodies for flow cytometry were obtained from Biolegend or eBioscience with the exception of CD107a (BD Bioscience). Flow cytometry was performed on either a BD Accuri, BD Facsverse, BD LRSII Fortessa or Beckman Coulter Cyan. Data was analysed on FlowJo Software. Fluorescence activated cell sorting (FACS) was undertaken on a MoFlo (Beckman Coulter) or FACS Aria (BD Bioscience).

CAR Detection

To stain for CAR expression a chimeric ROR1 protein fused to the murine IgG2a Fc domain was utilised and produced in stably transduced K562 cells. CD19 CAR expression was detected with the use of chimeric CD19 fused to Rabbit Fc. Secondary staining was with non-cross reactive anti-Fc antibodies from Jackson Immunolabs.

FACS Based Killing Assay

Target cells were transduced with eGFP to act as a marker and primary CLL cells were labelled with CFSE using standard protocols and were seeded at a density of 25,000 cells/well in a 96 well plate. They were cultured with effector cells in various effector to target ratio into a final volume of 200 µl and spun for 400 G for 5 minutes before being incubated at 37° C. and 5% $CO_2$. The next day 100 µl of supernatant was removed for cytokine ELISA, the plate stained with CD3 antibodies and fixable viability dye (eBioscience) and samples transferred to FACS tubes with identical amounts of Flowcheck Microsphere counting beads (Beckman Coulter). Data was acquired by flow cytometry gating for 1000 events in the counting beads gate.

5' Rapid Amplification of cDNA Ends (RACE)

Oligoclonal hybridomas from Aldevron GmBH were separated into single cell clones either by limited dilution or single cell sorting into 96 well plates and colonies grown until confluent (approximately 2 weeks). Supernatant was screened against ROR1 positive and negative cell lines to ensure the presence of a specific anti-ROR1 antibody and also used for isotyping using rat immunoglobulin isotyping kits (eBioscience or BD Bioscience).

Clones were grown until confluence in 6 well plates or 10 cm plates and then pelleted into RNAlater (Life Technologies) before RNA was extracted using RNA MiniPlus Kit (Qiagen). RNA was reverse transcribed to cDNA using Quantitect Reverse Transcriptase (Qiagen). An aliquot of this cDNA was assessed with GAPDH primers which were able to differentiate genomic and cDNA to ensure quality of samples. cDNA had a polyC tail added with Terminal Transferase (New England Biolabs) and nested PCR reactions were performed (Phusion Taq; New England Biolabs or Platinum Taq High Fidelity: Life Technologies) to identify the variable regions of the heavy and light chains, using primers specific for light chain isotype and heavy chain isotype.

PCR products were run on a 1% TBE gel and post-stained with Gelstar (Lonza). Bands of the correct size were extracted and sent for direct sequencing and inserted into Topo subcloning vectors (Life Technologies) for subsequent sequencing. To allow us to directly sequence the PCR products, primers were designed such that they bound further within the constant regions and allowed read through of the sequencing reactions without omission of the terminal variable region thereby obviating the need for Topo subcloning.

Sequence data was compared to the IMGT V-QUEST database of Rat germline immunoglobulin sequences and consensus sequences obtained that were productive and had an in frame signal sequence (Brochet et al., 2008, Alamyar et al., 2012). Overlap extension primers were designed to amplify the heavy and light chains whilst introducing a GGGGSGGGGSGGGGS (SEQ ID NO. 1) linker sequence to generate ScFv constructs. A secreted version of the ScFv was produced by cloning the ScFv sequence in frame with murine IgG2a constant region using NcoI and BamHI sites (or if needed the compatible BglII or BclI sites) and into the pCCL.PGK lentiviral backbone which included an extracellular spacer, 41BB and CD3ζ using SalI and BamHI sites. Antibodies were generated by cloning the heavy chain variable sequence in frame with human constant region and the light chain with the kappa constant region.

Example 2

ROR1 is Expressed on Primary CLL Cells

Primary CLL cells from peripheral blood of newly diagnosed and treated patients was analysed for expression of ROR1 by flow cytometry. ROR1 was detectable in all samples analysed (Biolegend Clone 2A2). Antigen density was assessed by Qifikit (Dako, Agilent Technologies). Median antigen binding capacity (ABC) for ROR1 was 2304 molecules/cell with a range of 800-4828 and CD19 was expressed at significantly higher levels with a median level of 12583 (Range 5894-23652). See Table 1 below.

TABLE 1

| Patient No. | ROR1 ABC | CD19 ABC |
| --- | --- | --- |
| 1 | 800 | 10751 |
| 2 | 835 | 11314 |
| 3 | 932 | 11423 |
| 4 | 1148 | 12685 |
| 5 | 1150 | 23652 |
| 6 | 1354 | 5894 |
| 7 | 1535 | 12680 |
| 8 | 1825 | 12486 |
| 9 | 2206 | 10307 |
| 10 | 2260 | 11027 |
| 11 | 2348 | 12481 |
| 12 | 2621 | 10026 |
| 13 | 2945 | 19176 |
| 14 | 3014 | 17734 |
| 15 | 3035 | 13488 |
| 16 | 3058 | 15593 |
| 17 | 3428 | 10149 |
| 18 | 4040 | 12864 |
| 19 | 4828 | 23268 |
| 20 | 3658 | 17797 |

Example 3

Immunization of Rats and Production of ROR1 Antibodies

Following immunisation of 3 rats with full length human ROR1 protein and DNA, we obtained 38 oligoclonal hybridomas. 17 of these were solved with 5' RACE to identify the variable regions of the heavy and light chain. We obtained sequences which coded for 13 novel antibodies (4 clones resulted in identical sequences being obtained) of which 10 bind in a Single Chain Variable Fragment (ScFv) format. (Cloning Hybridoma cDNA by RACE, Andrew Bradbury) See Table 2 below.

TABLE 2

| | Binding Domain | Binds as whole immunoglobulin | Binds in scFv format |
| --- | --- | --- | --- |
| Clone G3 | Ig | Yes | No |
| Clone G5 | Ig | Yes | Yes |
| Clone E7 | Ig | Yes | No |
| Clone J | Ig | Yes | No |
| Clone F | Fz | Yes | Yes |
| Clone B | Ig | Yes | Yes |
| Clone A | Ig | Yes | Yes |
| Clone I | Ig | Yes | Yes |
| Clone O | Ig | Yes | Yes |
| Clone Pi | Ig | Yes | Yes |
| Clone Mu | Ig | Yes | Yes |
| Clone R | Ig | Yes | Yes |
| Clone V | Between Ig and Fz | Yes | Yes |

As can be seen above, clone F binds the frizzled domain. All the other clones (except V) bound the immunoglobulin domain. The prior art antibodies R12 and 4A5 also bind the immunoglobulin domain. Therefore, clone F shows different and distinct binding characteristics compared to prior art antibodies R12 and 4A5.

Example 4

Isolation of Anti-ROR1 Antibody Sequences from Hybridoma

Antibody sequences were obtained by 5' Rapid Amplification of cDNA ends. Oligoclonal hybridomas from Aldevron GmBH were separated into single cell clones either by dilution or single cell sorting into 96 well plates and colonies grown until confluent (approximately 2 weeks). Supernatant was screened against ROR1 positive and negative cell lines to ensure the presence of a specific anti-ROR1 antibody and also used for isotyping using rat immunoglobulin isotyping kits (eBioscience or BD Bioscience).

Clones were grown until confluence in 6 well plates or 10 cm plates and then pelleted into RNAlater (Life Technologies) before RNA was extracted using RNA MiniPlus Kit (Qiagen). RNA was reverse transcribed to cDNA using Quantitect Reverse Transcriptase (Qiagen). An aliquot of this cDNA was assessed with GAPDH primers which were able to differentiate genomic and cDNA to ensure quality of samples. cDNA had a polyC tail added with Terminal Transferase (New England Biolabs) and nested PCR reactions were performed (Phusion Taq; New England Biolabs or Platinum Taq High Fidelity: Life Technologies) to identify the variable regions of the heavy and light chains, using primers specific for light chain isotype and heavy chain isotype.

PCR products were run on a 1% TBE gel and post-stained with Gelstar (Lonza). Bands of the correct size were extracted and sent for direct sequencing or inserted into Topo subcloning vectors (Life Technologies) for subsequent sequencing.

Sequence data was compared to the IMGT V-QUEST database of Rat germline immunoglobulin sequences and consensus sequences obtained that were productive and had an in frame signal sequence (Brochet et al., 2008, Alamyar et al., 2012). Overlap extension primers were designed to amplify the heavy and light chains whilst introducing a linker sequence to generate ScFv constructs.

A secreted version of the ScFv was produced by cloning the ScFv sequence in frame with murine IgG2a constant region using NcoI and BamHI sites (or if needed the compatible BglII or BclI sites).

ROR1 antibodies were generated by cloning the variable sequence in frame with human or mouse heavy chain constant region and light chain with the corresponding human or mouse kappa constant region.

Example 5

Humanization of Rat scFvs

Based on superior cytotoxicity and function, clones A and F were selected for humanization. The variable domain sequences of rat scFvs were searched against the human IgG germline database. Five human framework sequences with high homology to each rat antibody were chosen as human acceptors for both light and heavy chains CDRs. The sequences of five humanized VLs and humanized VHs were obtained after directly grafting the CDRs of each rat antibody to the human acceptor frameworks.

Example 6

Cytotoxicity of Novel ScFv Based CAR T Cells

T-cells transduced to express the CAR were co-cultured with SupT1-ROR1 cells and resulted in significant cytotoxicity irrespective of the ScFv used, which was not seen with the corresponding ROR1 negative cell line. We concurrently tested the same T-cells against SKW6.4 cells, which express low levels of ROR1 similar to CLL cells as opposed to the SupT1-ROR1 cell line which has been transduced to express high levels of ROR1. In this case only Clone F bearing T-cells were able to kill target cells in a comparable range to CD19 based CAR T-cells. See FIG. 2.

Example 7

CD107a Degranulation Assay

To corroborate the co-culture data we undertook a CD107a assay, which assesses surface expression of a lysosomal associated membrane protein (LAMP-1) usually present in cytoplasmic granule membranes but which translocate to the cell surface following T-cell activation at the time of activation. Against ROR1 high cells lines (SupT1_ROR1), CD107a degranulation was comparable irrespective of ScFv. However against SKW cells (ROR1 Low) Clone F consistently showed higher levels of CD07a expression (43% for F vs 14% for Pi vs 2% for UT) implying that the higher levels of target killing was in part mediated by improved cytotoxic granule release.

Example 8

Optimisation of the Extracellular Spacer

The previously generated constructs contained the CD8a spacer (81 amino acids (AA)) which was substituted for a full length IgG spacer (239 AA), IgG1 hinge only spacer (19 AA) or a short linker sequence (9 AA) which included the amino acid sequence GGGGS (SEQ ID NO. 2) in an attempt to allow flexibility of the ScFv on the cell surface membrane. See FIG. 3.

T-cells transduced with these different spacer sequences showed marked difference in their ability to kill target cells which was consistent against cell lines expressing high and low levels of ROR1. Interestingly Clone A and Clone F showed a reciprocal relationship with the longest IgG spacer still showing moderate efficacy for Clone F but poor killing for Clone A, which was reversed with the shortest linker spacer. This undoubtedly has to do with the optimum distance generated between target cell antigen epitope and the T-cell CAR structure.

Given that changing the spacers resulted in differences in cytotoxicity and the finding that the hinge spacer seemed optimal for both clones A and F, we substituted the hinge spacer into all of the ScFv constructs and repeated the cytotoxicity assessment.

T-cells transduced with hinge spacer constructs showed no cytotoxicity against SupT1 ROR1 negative cells, but led to almost complete killing of SupT1 ROR1 positive cells at 24 hours, with the exception of clone V and this was consistent on repeated experiments.

Interestingly, the hinge spacer improved cytotoxicity against SKW6.4 cells for all ScFv constructs even when the effector to target ratio was reduced to 1:1. For example for the R12 ScFv the average percentage of target cells remaining with the CD8α spacer was 80% compared to 40% with the hinge spacer. See FIG. 4.

Example 9

Cytotoxicity Against Primary CLL Cells

ROR1 CAR T-cells with a hinge spacer and 41BB and CD3zeta intracellular signalling domains were generated to express the ScFv sequences of FIG. 5.

At 1:1 Effector:Target ratio in a FACS based killing assay Clones A and F showed superior killing against R12, V and Mu against SKW6.4 cell lines.

Example 10

Comparison with CD19 ScFv Based CAR

T-cells expressing a 2nd generation CAR against ROR1 (Clone A and Clone F) were produced along with a CD19 ScFv CAR (based on the fmc63 ScFv). A 1:1 Effector:Target FACS based killing assay showed that Clone A and F had similar levels of cytotoxicity compared to CD19 based ScFv. This is an important finding as in SKW cells (as well as primary CLL cells) ROR1 is expressed at much lower levels compared to CD19.

Example 11

In Vivo Modelling of ROR1 CAR T Cells

To assess the in vivo function of our newly developed ScFv sequences in CAR format we undertook a murine model utilising Jekol cells transduced to express firefly luciferase. $0.5 \times 10^6$ cells were injected by tail vein into NSG mice NOD.Cg-Prkdc$^{scid}$ Il2rg$^{tm1Wjl}$/SzJ. On day 7, $4 \times 10^7$ transduced T cells were injected by tail vein expressing either only the mCherry transduction marker, R12 ScFv CAR, Clone A ScFv CAR, Clone F ScFv CAR, CD19 fmc63 CAR or the non-specific GD2 CAR.

Treatment with CAR T cells with Clone A and F based ScFv provided protection against tumour progression in keeping with R12. See FIG. 6.

Example 12

Epitope Mapping

To assess the epitope of the generated antibodies we produced cell lines with truncated ROR1: these comprised SUPT1 cells expressing full length ROR1 (Immunoglobulin domain, Frizzled domain and Kringle Domain), Immunoglobulin only SupT1, Frizzled Only SupT1, Kringle Only SupT1 and combinations (Ig and Frizzled SupT1 and Frizzled and Kringle SupT1). This demonstrated that Clone F bound to the Frizzled domain, Clone V bound to between the Ig and Frizzled domain and all of the other clones bound the Ig domain.

To further characterize the epitope that Clone F bound specifically we compared rat ROR1 to human ROR1 to assess differences in amino acid between these two species. We made a number of mutated human ROR1 constructs that included single amino acid substitutions to putative amino acids that these antibodies could bind to further characterize the epitope in question.

For clone F, point mutations were generated for the Fz domain of human ROR1 at positions 254 and 261. The particular mutations used were I(254)V and Q(261)H.

It was found that the Q(261)H substitution reduced or stopped the clone F antibody binding to ROR1-Fz domain, whereas the I(254)V substitution did not seem to affect binding. Further, the combination of Q(261)H and I(254)V also prevented antibody binding. Therefore, Gln-261 is essential for antibody binding. Results can be seen in FIG. 7.

Example 13

Clone F is Unique to Other Antibodies Generated (Murine and Rabbit) Because of Sequence Homology Human, murine, rabbit and rat ROR1 protein sequences were aligned using Uniprot web based software (http://www.uniprot.org/align/) and the variation between the different species highlighted. Uniprot accession numbers: Human (Q01973), Murine (Q9Z139) and Rabbit (G1U5L1). For rat ROR1, NCBI reference sequence NP 001102141.1 was used as the corresponding Uniprot sequence was only partially complete.

Clone F binds to Q261, which was possible due to differences between rat and human amino acids at this position (the human amino acid at position 261 is glutamine (Q) whereas the corresponding amino acid at this position in rat is histidine (H)). When rats are immunised with human ROR1, this amino acid difference is recognised as an immunogen relative to the rat ROR1 sequence, against which an antibody is produced.

The known antibody R12 (rabbit) and murine ROR1 binders show homology with human ROR1 at this site (i.e. they all have glutamine (Q) at this position). As a result, immunisation of rabbits or mice with human ROR1 does not result in antibody production directed to this position as it is not immunogenic. In view of this, clone F is unique in its ability to bind to this epitope.

Example 14

Cytotoxicity of Humanised ScFv Based CAR T Cells

We generated humanised variants of Clone F and obtained five novel humanised light chains (hVL1-5) and five novel humanised heavy chains (hVH1-5). Using overlap extension PCR, we cloned these constructs into a ScFv format (Signal Peptide, Heavy, Linker and Light Chain) resulting in 25 constructs for Clone F in which each light chain was paired with each heavy chain. These humanised ScFv sequences were cloned in frame to a murine IgG2a constant region to yield a fusion protein comprising the ScFv with the murine IgG2a constant region. We cloned this into the SFG retroviral cassette and generated supernatant containing the ScFv fusion proteins for Clone F.

We screened the supernatant containing the ScFv fusion proteins against cell lines expressing just the Frizzled domain of ROR1 (which clone F binds to). Supernatant was added to a mixture of the above cells which could be differentiated by their expression of GFP (Immunoglobulin Cells GFP negative and Frizzled Cells GFP positive). Supernatant was left for 30 minutes before cells were washed and APC anti-murine IgG added (to detected the IgG2a component of the fusion protein).

Of the 25 humanised constructs, three bound particularly well. These three humanised constructs as well as a control were cloned into a lentiviral backbone and viral supernatant was produced to generate CAR T-cells expressing these novel humanised ScFvs. These T-cells were co-cultured with SupT1 cells (ROR1 negative) as well as SupT1-ROR1, SKW and Jekol cells and CD107a degranulation assessed. We utilised an mCherry marker to ensure we assessed CD107a degranulation only in the transduced cells.

41

This demonstrated that all three humanised ScFv for Clone F had significant degranulation in response to target cells as demonstrated by a shift above that of background. We included the parental rat ScFv constructs as a comparator as well as a control humanised construct that did not bind ROR1.

Example 15

Cytotoxicity Against Solid Tumour Cells Lines

ROR1 positive solid tumour cell lines representative of a range of malignancies were co-cultured with ROR1 CAR T-cells for 24 hours. Cytotoxicity was assessed with a MTS assay at 24 hours and IFNγ measured. Clone F candidates demonstrated significant cytotoxicity against target cells with consequent IFNγ secretion. Further, T-cell clustering and proliferation was seen with the candidates but not un-transduced or control CAR T-cells against PANC-1 cells.

Based on the CD107a degranulation assay, ScFv constructs that resulted in CD107a degranulation were chosen for a formal cytotoxicity assay against SKW6.4, PCL12, Raji and Jekol cells, all of which express ROR1 as previously described.

Co-culture of T-cells expressing one of the humanised constructs showed similar levels of cytotoxicity compared to the parental Clone F. Cytotoxicity was compared to T-cells transduced to express a GD2 specific CAR as control.

To compare off target toxicity with humanised F we undertook a prolonged co-culture with PANC1 cells (ROR1 positive) and MCF7 cells (ROR1 negative). We utilised the CD19 fmc63 CAR as an internal control. The hF was able to kill PANC1 cells as would be expected.

We generated ROR1-CAR T-cells using our optimal humanised F clone and compared cytotoxicity against a panel of ROR1 positive cell lines which constitutively express ROR1 representative of ALL (697, Kasumi2), Lymphoma (Jekol, Raji), CLL (SKW, PCL12) and demonstrated superior cytotoxicity compared to comparative ROR1 ScFvs (R12 and 4A5). See FIG. 8.

CD19fmc63 and hF, R12, 4A5 ROR1 CAR T-cells were generated as previously described. These were co-cultured with primary CLL cells which had been CFSE labelled and isolated using a B-CLL isolation kit (Miltenyi Bioscience) in a 4:1 Effector:Target ratio. Cytotoxicity was assessed at 24 hours by comparing viable CLL cells left in the co-culture compared to CLL cells co-cultured with a control GD2 CAR.

hF resulted in superior cytotoxicity compared to R12 and 4A5 ROR1 CAR T-cells. Cytotoxicity was lower compared to CD19 CAR T-cells in keeping with the lower antigen density of ROR1 compared to CD19. See FIG. 9.

Example 16

Clone F ROR-1 CAR T Cells Lead to Significant Cytotoxicity of ROR1 Positive Neuroblastoma Cell Lines ROR1 CAR T cells lead to significant cytotoxicity of NB-1643 and NB-7 ROR1+ neuroblastoma cell lines but not Rh30 ROR1 negative cell lines at 5:1 and 10:1 target to effector ratios at 24 and 48 hours (see FIG. 10).

Example 17

Clone F ROR-1 CAR T Cells Compared to CD19 CAR T Cells

Clone F ROR1 CAR T Cells lead to significant IFNg secretion at 24 hours compared to control non-targeting CD19 CART cells against ROR1 positive (1643, PANC1 and NB-7) cell lines but not Rh30 ROR1 negative cells (see FIG. 11).

Example 18

Clone F CAR T-Cells Demonstrate Superiority Compared to Known CAR T-Cells

The first description of a CAR targeting ROR1 utilised the 2A2 scFv (Hudecek et al., 2010) and subsequently this was compared to both R11 and R12 scFv derived CAR T cells, with R12 being the best (Hudecek et al., 2013). We have shown that Clone F is superior to the R12 lead construct by this group in terms of cytotoxicity and with a differential cytokine release pattern. Therefore, the Clone F construct is also superior to 2A2 and R11.

The UCSD group generated ROR1 antibodies D10, H10 and 4A5. Their lead construct was 4A5 and this data has been published (Deniger et al., 2015). Our Clone F CAR has been compared to 4A5 and shows superior cytotoxicity and cytokine secretion. Given this, the Clone F construct is also superior to D10 and H10. In addition, the D10 and H10 antibodies were generated following murine immunisation and thus will not bind to the same epitope as Clone F.

Example 19

Humanization of Clone F Imparts Advantages Compared to Non-Humanised Comparator Constructs One of the rationales for targeting ROR1 as opposed to CD19, is sparing of the normal ROR1 negative B cell population. However at the same time, continued presence of normal CD19+ B cells allows for immune responses directed against a rat derived scFv. This has been seen with murine scFvs and have led to clinically significant outcomes, including anaphylaxis with mRNA modified mesothelin CART cells (Maus et al., 2013) or antibody responses, with α-folate receptor or carbonic anhydrase IX specific CAR T cells (Lamers et al., 2006, Kershaw et al., 2006). T cell mediated immune responses are also possible due to cross presentation of components of the CAR on MHC. CD19 CAR T cells by comparison, inherently neutralize the risk of antibody based immune responses by eradicating the normal B cell population, with B cell recurrence associated with a higher risk of relapse.

By undertaking humanization of Clone F we have decreased the likelihood of immune responses against the CAR leading to enhanced persistence and decreased immunogenicity.

SEQUENCE LISTING

The amino acid sequences listed below are shown using standard one letter codes for amino acids. The sequences are for clone F and the five humanised variable sequences that were developed.

The variable regions of the heavy and light chains of Clone F described above and the humanised versions of this clone are as follows:

```
Clone F light chain variable region
                                        (SEQ ID NO. 3)
DIQMTQSPSFLSASVGDRVTINCKASQNIDRYLNWYQQKLGEAPKRLLYNT

NKLQTGIPSRFSGSGSATDFTLTISSLQPEDFATYFCLQYNSLPLTFGSGT

KLEIK
```

-continued

Humanised 1 light chain variable region
(SEQ ID NO. 4)
DIQMTQSPSSLSASVGDRVTITCKAS<u>QNIDRY</u>LNWYQQKPGKAPKRLIY<u>NT
N</u>KLQTGVPSRFSGSGSGTEFTLTISSLQPEDFATYYC<u>LQYNSLPLT</u>FGQGT
KLEIK Humanised 2 light chain variable region
(SEQ ID NO. 5)
DIQMTQSPSSLSASVGDRVTITCKAS<u>QNIDRY</u>LNWFQQKPGKAPKSLIY<u>NT
N</u>KLQTGVPSKFSGSGSGTDFTLTISSLQPEDFATYYC<u>LQYNSLPLT</u>FGQGT
RLEIK Humanised 3 light chain variable region
(SEQ ID NO. 6)
DIQMTQSPSSLSASVGDRVTITCKAS<u>QNIDRY</u>LNWYQQKPGKAPKLLIY<u>NT
N</u>KLQTGVPSRFSGSGSGTDFTLTISSLQPEDFATYYC<u>LQYNSLPLT</u>FGQGT
KLEIK Humanised 4 light chain variable region
(SEQ ID NO. 7)
DIQLTQSPSFLSASVGDRVTITCKAS<u>QNIDRY</u>LNWYQQKPGKAPKLLIY<u>NT
N</u>KLQTGVPSRFSGSGSGTEFTLTISSLQPEDFATYYC<u>LQYNSLPLT</u>FGQGT
KLEIK Humanised 5 light chain variable region
(SEQ ID NO. 8)
DIQMTQSPSTLSASVGDRVTITCKAS<u>QNIDRY</u>LNWYQQKPGKAPKLLIY<u>NT
N</u>KLQTGVPSRFSGSGSGTEFTLTISSLQPDDFATYYC<u>LQYNSLPLT</u>FGQGT
KLEIK Clone F heavy chain variable region
(SEQ ID NO. 9)
EVQLVESGGGLVQPGRSLKLSCAAS<u>GFIFSEHN</u>MAWVRQAPKKGLEWVAT<u>I
SDDGRNT</u>YYRDSMRGRFTISRENARSTLYLQLDSLRSEDTATYYC<u>ASHRYN
LFDS</u>WGQGVMVTVSS Humanised 1 heavy chain variable region
(SEQ ID NO. 10)
QVQLVESGGGVVQPGRSLRLSCAAS<u>GFIFSEHN</u>MAWVRQAPGKGLEWVAT<u>I
SDDGRNT</u>YYRDSMRGRFTISRDNSKNTLYLQMNSLRAEDTAVYYC<u>TSHRYN
LFDS</u>WGQGTMVTVSS Humanised 2 heavy chain variable region
(SEQ ID NO. 11)
EVQLVESGGGLVQPGGSLRLSCAAS<u>GFIFSEHN</u>MAWVRQAPGKGLEWVST<u>I
SDDGRNT</u>YYRDSMRGRFTISRDNSKNTLYLQMNSLRAEDTAVYYC<u>AKHRYN
LFDS</u>WGQGTLVTVSS Humanised 3 heavy chain variable region
(SEQ ID NO. 12)
EVQLVESGGGLVQPGGSLRLSCAAS<u>GFIFSEHN</u>MAWVRQAPGKGLEWVAT<u>I
SDDGRNT</u>YYRDSMRGRFTISRDNAKNSLYLQMNSLRAEDTAVYYC<u>ARHRYN
LFDS</u>WGQGTMVTVSS Humanised 4 heavy chain variable region
(SEQ ID NO. 13)
EVQLVESGGGLVQPGGSLRLSCAAS<u>GFIFSEHN</u>MAWVRQAPGKGLVWVST<u>I
SDDGRNT</u>YYRDSMRGRFTISRDNAKNTLYLQMNSLRAEDTAVYYC<u>ARHRYN
LFDS</u>WGQGTLVTVSS Humanised 5 heavy chain variable region
(SEQ ID NO. 14)
EVQLVESGGGLVQPGRSLRLSCAAS<u>GFIFSEHN</u>MAWVRQAPGKGLEWVST<u>I
SDDGRNT</u>YYRDSMRGRFTISRDNAKNSLYLQMNSLRAEDTALYYC<u>AKHRYN
LFDS</u>WGQGTLVTVSS The three CDR sequences in each of the variable regions above are underlined. These CDR sequences have been determined based on information on framework regions and CDRs from the IMGT (the international ImMunoGeneTics information system) database (see www.imgt.org).

Further sequences related to those above and their relevant sequence identifier numbers (SED ID NOs) are given below:

| Sequence | Description | SEQ ID NO: |
|---|---|---|
| DIQMTQSPSFLSASVGDRVTINCKAS | Rat Light Chain Framework Region 1 | 15 |
| QNIDRY | Rat Light Chain CDR1 | 16 |
| LNWYQQKLGEAPKRLLY | Rat Light Chain Framework Region 2 | 17 |
| NTN | Rat Light Chain CDR2 | 18 |
| KLQTGIPSRFSGSGSATDFTLTISSLQPEDFATYFC | Rat Light Chain Framework Region 3 | 19 |
| LQYNSLPLT | Rat Light Chain CDR3 | 20 |
| FGSGTKLEIK | Rat Light Chain Framework Region 4 | 21 |
| EVQLVESGGGLVQPGRSLKLSCAAS | Rat Heavy Chain Framework Region 1 | 22 |
| GFIFSEHN | Rat Heavy Chain CDR1 | 23 |
| MAWVRQAPKKGLEWVAT | Rat Heavy Chain Framework Region 2 | 24 |
| ISDDGRNT | Rat Heavy Chain CDR2 | 25 |
| YYRDSMRGRFTISRENARSTLYLQLDSLRSEDTATYYC | Rat Heavy Chain Framework Region 3 | 26 |
| ASHRYNLFDS | Rat Heavy Chain CDR3 | 27 |

| Sequence | Description | SEQ ID NO: |
|---|---|---|
| WGQGVMVTVSS | Rat Heavy Chain Framework Region 4 | 28 |
| DIQMTQSPSSLSASVGDRVTITCKAS | Humanised 1 Light Chain FW Region 1 | 29 |
| QNIDRY | Humanised 1 Light Chain CDR1 | 16 |
| LNWYQQKPGKAPKRLIY | Humanised 1 Light Chain FW Region 2 | 30 |
| NTN | Humanised 1 Light Chain CDR2 | 18 |
| KLQTGVPSRFSGSGSGTEFTLTISSLQPEDFATYYC | Humanised 1 Light Chain FW Region 3 | 31 |
| LQYNSLPLT | Humanised 1 Light Chain CDR3 | 20 |
| FGQGTKLEIK | Humanised 1 Light Chain FW Region 4 | 32 |
| QVQLVESGGGVVQPGRSLRLSCAAS | Humanised 1 Heavy Chain FW Region 1 | 33 |
| GFIFSEHN | Humanised 1 Heavy Chain CDR1 | 23 |
| MAWVRQAPGKGLEWVAT | Humanised 1 Heavy Chain FW Region 2 | 34 |
| ISDDGRNT | Humanised 1 Heavy Chain CDR2 | 25 |
| YYRDSMRGRFTISRDNSKNTLYLQMNSLRAEDTAVYYCTS | Humanised 1 Heavy Chain FW Region 3 | 35 |
| TSHRYNLFDS | Humanised 1 Heavy Chain CDR3 | 36 |
| WGQGTMVTVSS | Humanised 1 Heavy Chain FW Region 4 | 37 |
| DIQMTQSPSSLSASVGDRVTITCKAS | Humanised 2 Light Chain FW Region 1 | 29 |
| QNIDRY | Humanised 2 Light Chain CDR1 | 16 |
| LNWFQQKPGKAPKSLIY | Humanised 2 Light Chain FW Region 2 | 38 |
| NTN | Humanised 2 Light Chain CDR2 | 18 |
| KLQTGVPSKFSGSGSGTDFTLTISSLQPEDFATYYC | Humanised 2 Light Chain FW Region 3 | 39 |
| LQYNSLPLT | Humanised 2 Light Chain CDR3 | 20 |
| FGQGTRLEIK | Humanised 2 Light Chain FW Region 4 | 40 |
| EVQLVESGGGLVQPGGSLRLSCAAS | Humanised 2 Heavy Chain FW Region 1 | 41 |
| GFIFSEHN | Humanised 2 Heavy Chain CDR1 | 23 |
| MAWVRQAPGKGLEWVST | Humanised 2 Heavy Chain FW Region 2 | 42 |
| ISDDGRNT | Humanised 2 Heavy Chain CDR2 | 25 |
| YYRDSMRGRFTISRDNSKNTLYLQMNSLRAEDTAVYYCAK | Humanised 2 Heavy Chain FW Region 3 | 43 |
| AKHRYNLFDS | Humanised 2 Heavy Chain CDR3 | 44 |
| WGQGTLVTVSS | Humanised 2 Heavy Chain FW Region 4 | 45 |
| DIQMTQSPSSLSASVGDRVTITCKAS | Humanised 3 Light Chain FW Region 1 | 29 |
| QNIDRY | Humanised 3 Light Chain CDR1 | 16 |
| LNWYQQKPGKAPKLLIY | Humanised 3 Light Chain FW Region 2 | 46 |
| NTN | Humanised 3 Light Chain CDR2 | 18 |
| KLQTGVPSRFSGSGSGTDFTLTISSLQPEDFATYYC | Humanised 3 Light Chain FW Region 3 | 47 |
| LQYNSLPLT | Humanised 3 Light Chain CDR3 | 20 |
| FGQGTKLEIK | Humanised 3 Light Chain FW Region 4 | 32 |
| EVQLVESGGGLVQPGGSLRLSCAAS | Humanised 3 Heavy Chain FW Region 1 | 41 |

| Sequence | Description | SEQ ID NO: |
|---|---|---|
| GFIFSEHN | Humanised 3 Heavy Chain CDR1 | 23 |
| MAWVRQAPGKGLEWVAT | Humanised 3 Heavy Chain FW Region 2 | 34 |
| ISDDGRNT | Humanised 3 Heavy Chain CDR2 | 25 |
| YYRDSMRGRFTISRDNAKNSLYLQMNSLRAEDTAV YYCAR | Humanised 3 Heavy Chain FW Region 3 | 48 |
| ARHRYNLFDS | Humanised 3 Heavy Chain CDR3 | 49 |
| WGQGTMVTVSS | Humanised 3 Heavy Chain FW Region 4 | 37 |
| DIQLTQSPSFLSASVGDRVTITCKAS | Humanised 4 Light Chain FW Region 1 | 50 |
| QNIDRY | Humanised 4 Light Chain CDR1 | 16 |
| LNWYQQKPGKAPKLLIY | Humanised 4 Light Chain FW Region 2 | 46 |
| NTN | Humanised 4 Light Chain CDR2 | 18 |
| KLQTGVPSRFSGSGSGTEFTLTISSLQPEDFATYYC | Humanised 4 Light Chain FW Region 3 | 31 |
| LQYNSLPLT | Humanised 4 Light Chain CDR3 | 20 |
| FGQGTKLEIK | Humanised 4 Light Chain FW Region 4 | 32 |
| EVQLVESGGGLVQPGGSLRLSCAAS | Humanised 4 Heavy Chain FW Region 1 | 41 |
| GFIFSEHN | Humanised 4 Heavy Chain CDR1 | 23 |
| MAWVRQAPGKGLVWVST | Humanised 4 Heavy Chain FW Region 2 | 51 |
| ISDDGRNT | Humanised 4 Heavy Chain CDR2 | 25 |
| YYRDSMRGRFTISRDNAKNTLYLQMNSLRAEDTAV YYCAR | Humanised 4 Heavy Chain FW Region 3 | 52 |
| ARHRYNLFDS | Humanised 4 Heavy Chain CDR3 | 49 |
| WGQGTLVTVSS | Humanised 4 Heavy Chain FW Region 4 | 45 |
| DIQMTQSPSTLSASVGDRVTITCKAS | Humanised 5 Light Chain FW Region 1 | 53 |
| QNIDRY | Humanised 5 Light Chain CDR1 | 16 |
| LNWYQQKPGKAPKLLIY | Humanised 5 Light Chain FW Region 2 | 46 |
| NTN | Humanised 5 Light Chain CDR2 | 18 |
| KLQTGVPSRFSGSGSGTEFTLTISSLQPDDFATYYC | Humanised 5 Light Chain FW Region 3 | 54 |
| LQYNSLPLT | Humanised 5 Light Chain CDR3 | 20 |
| FGQGTKLEIK | Humanised 5 Light Chain FW Region 4 | 32 |
| EVQLVESGGGLVQPGRSLRLSCAAS | Humanised 5 Heavy Chain FW Region 1 | 55 |
| GFIFSEHN | Humanised 5 Heavy Chain CDR1 | 23 |
| MAWVRQAPGKGLEWVST | Humanised 5 Heavy Chain FW Region 2 | 42 |
| ISDDGRNT | Humanised 5 Heavy Chain CDR2 | 25 |
| YYRDSMRGRFTISRDNAKNSLYLQMNSLRAEDTAL YYCAK | Humanised 5 Heavy Chain FW Region 3 | 56 |
| AKHRYNLFDS | Humanised 5 Heavy Chain CDR3 | 44 |
| WGQGTLVTVSS | Humanised 5 Heavy Chain FW Region 4 | 45 |
| XXHRYNLFDS (where $X_1$ is A or T and $X_2$ is S, K or R) | General Heavy Chain CDR3 | 57 |

An alternative method for labelling CDRs is using the Kabat system and this can give slightly different results. However, this can easily be determined by someone skilled in the art. For the avoidance of doubt, the CDR sequences in the variable regions based on the Kabat system are as follows, where the Kabat CDRs are in bold:

Clone F light chain variable region
(SEQ ID NO. 3)
DIQMTQSPSFLSASVGDRVTINCKASQNIDRYLNWYQQKLGEAPKRLLY**NT
NKLQTGIPSRFSGSGSATDFTLTISSLQPEDFATYFCLQYNSLPLT**FGSGT
KLEIK Humanised 1 light chain variable region
(SEQ ID NO. 4)
DIQMTQSPSSLSASVGDRVTITCKASQNIDRYLNWYQQKPGKAPKRLIY**NT
NKLQTGVPSRFSGSGSGTEFTLTISSLQPEDFATYYCLQYNSLPLT**FGQGT
KLEIK Humanised 2 light chain variable region
(SEQ ID NO. 5)
DIQMTQSPSSLSASVGDRVTITCKASQNIDRYLNWFQQKPGKAPKSLIY**NT
NKLQTGVPSKFSGSGSGTDFTLTISSLQPEDFATYYCLQYNSLPLT**FGQGT
RLEIK Humanised 3 light chain variable region
(SEQ ID NO. 6)
DIQMTQSPSSLSASVGDRVTITCKASQNIDRYLNWYQQKPGKAPKLLIY**NT
NKLQTGVPSRFSGSGSGTDFTLTISSLQPEDFATYYCLQYNSLPLT**FGQGT
KLEIK Humanised 4 light chain variable region
(SEQ ID NO. 7)
DIQLTQSPSFLSASVGDRVTITCKASQNIDRYLNWYQQKPGKAPKLLIY**NT
NKLQTGVPSRFSGSGSGTEFTLTISSLQPEDFATYYCLQYNSLPLT**FGQGT
KLEIK Humanised 5 light chain variable region
(SEQ ID NO. 8)
DIQMTQSPSTLSASVGDRVTITCKASQNIDRYLNWYQQKPGKAPKLLIY**NT
NKLQTGVPSRFSGSGSGTEFTLTISSLQPDDFATYYCLQYNSLPLT**FGQGT
KLEIK Clone F heavy chain variable region
(SEQ ID NO. 9)
EVQLVESGGGLVQPGRSLKLSCAASGFIFSEHNMAWVRQAPKKGLEWVATI
SDDGRNTYYRDSMRGRFTISRENARSTLYLQLDSLRSEDTATYYCAS**HRYN
LFDS**WGQGVMVTVSS Humanised 1 heavy chain variable region
(SEQ ID NO. 10)
QVQLVESGGGVVQPGRSLRLSCAASGFIFSEHNMAWVRQAPGKGLEWVATI
SDDGRNTYYRDSMRGRFTISRDNSKNTLYLQMNSLRAEDTAVYYCTS**HRYN
LFDS**WGQGTMVTVSS Humanised 2 heavy chain variable region
(SEQ ID NO. 11)
EVQLVESGGGLVQPGGSLRLSCAASGFIFSEHNMAWVRQAPGKGLEWVSTI
SDDGRNTYYRDSMRGRFTISRDNSKNTLYLQMNSLRAEDTAVYYCAK**HRYN
LFDS**WGQGTLVTVSS Humanised 3 heavy chain variable region
(SEQ ID NO. 12)
EVQLVESGGGLVQPGGSLRLSCAASGFIFSEHNMAWVRQAPGKGLEWVATI
SDDGRNTYYRDSMRGRFTISRDNAKNSLYLQMNSLRAEDTAVYYCAR**HRYN
LFDS**WGQGTMVTVSS Humanised 4 heavy chain variable region
(SEQ ID NO. 13)
EVQLVESGGGLVQPGGSLRLSCAASGFIFSEHNMAWVRQAPGKGLVWVSTI
SDDGRNTYYRDSMRGRFTISRDNAKNTLYLQMNSLRAEDTAVYYCAR**HRYN
LFDS**WGQGTLVTVSS Humanised 5 heavy chain variable region
(SEQ ID NO. 14)
EVQLVESGGGLVQPGRSLRLSCAASGFIFSEHNMAWVRQAPGKGLEWVSTI
SDDGRNTYYRDSMRGRFTISRDNAKNSLYLQMNSLRAEDTALYYCAK**HRYN
LFDS**WGQGTLVTVSS Therefore, the CDRs when determined using the Kabat system are as follows:

| Sequence | Description | SEQ ID NO: |
| --- | --- | --- |
| KASQNIDRYLN | Light Chain CDR1 | 58 |
| NTNKLQT | Light Chain CDR2 | 59 |
| LQYNSLPLT | Light Chain CDR3 | 20 |
| EHNMA | Heavy Chain CDR1 | 60 |
| TISDDGRNTYYRDSMRG | Heavy Chain CDR2 | 61 |
| HRYNLFDS | Heavy Chain CDR3 | 62 |

The invention claimed is:

1. A chimeric antigen receptor (CAR) which comprises an antigen binding domain which selectively binds to Receptor Tyrosine Kinase Like Orphan Receptor 1 (ROR1), wherein the antigen binding domain comprises a light chain variable domain and a heavy chain variable domain, wherein the light chain variable domain comprises a light chain complementarity determining region (LCDR)1, an LCDR2 and an LCDR3, wherein LCDR1 comprises the amino acid sequence set forth in SEQ ID NO: 16; LCDR2 comprises the amino acid sequence set forth in SEQ ID NO: 18; and LCDR3 comprises the amino acid sequence set forth in SEQ ID NO: 20; and wherein the heavy chain variable domain comprises a heavy chain complementarity determining region (HCDR)1, an HCDR2 and an HCDR3, wherein HCDR1 comprises the amino acid sequence set forth in SEQ ID NO: 23; HCDR2 comprises the amino acid sequence set forth in SEQ ID NO: 25; and HCDR3 comprises the amino acid sequence selected from any of the sequences set forth in SEQ ID NOs: 27, 36, 44 and 49;

or wherein the light chain variable domain comprises a light chain complementarity determining region (LCDR)1, an LCDR2 and an LCDR3, wherein LCDR1 comprises the amino acid sequence set forth in SEQ ID NO: 58; LCDR2 comprises the amino acid sequence set forth in SEQ ID NO: 59; and LCDR3 comprises the amino acid sequence set forth in SEQ ID NO: 20; and wherein the heavy chain variable domain comprises a heavy chain complementarity determining region (HCDR)1, an HCDR2 and an HCDR3, wherein HCDR1 comprises the amino acid sequence set forth in SEQ ID NO: 60; HCDR2 comprises the amino acid sequence set forth in SEQ ID NO: 61; and HCDR3 comprises the amino acid sequence set forth in SEQ ID NO: 62.

2. The CAR of claim 1, wherein:

(a) the antigen binding domain has a light chain variable domain which comprises a Light Chain Framework Region (LCFR)1 comprising the amino acid sequence as set forth as one of SEQ ID NOs: 15, 29, 50 and 53; an LCFR2 comprising the amino acid sequence as set forth as one of SEQ ID NOs: 17, 30, 38 and 46; an LCFR3 comprising the amino acid sequence as set forth as one of SEQ ID NOs: 19, 31, 39, 47 and 54; and an LCFR4 comprising the amino acid sequence as set forth as one of SEQ ID NOs: 21, 32 and 40, wherein the sequence of each framework region may differ from the given sequence at up to five amino acid positions; or (b) the antigen binding domain has a light chain variable domain which comprises an LCFR1 comprising the amino acid sequence as set forth as one of SEQ ID NOs: 29, 50 and 53; an LCFR2 comprising the amino acid sequence as set forth as one of SEQ ID NOs: 30, 38 and 46; an LCFR3 comprising the amino acid sequence as set forth as one of SEQ ID NOs: 31, 39, 47 and 54; and an LCFR4 comprising the amino acid sequence as set forth as one of SEQ ID NOs: 32 and 40, wherein the sequence of each framework region may differ from the given sequence at up to five amino acid positions.

3. The CAR of claim 1, wherein:

(a) the antigen binding domain has a heavy chain variable domain which comprises a Heavy Chain Framework Region (HCFR)1 comprising the amino acid sequence as set forth as one of SEQ ID NOs: 22, 33, 41 and 55; an HCFR2 comprising the amino acid sequence as set forth as one of SEQ ID NOs: 24, 34, 42 and 51; an HCFR3 comprising the amino acid sequence as set forth as one of SEQ ID NOs: 26, 35, 43, 48, 52 and 56; and an HCFR4 comprising the amino acid sequence as set forth as one of SEQ ID NOs: 28, 37 and 45, wherein the sequence of each framework region may differ from the given sequence at up to five amino acid positions; or (b) the antigen binding domain may have a heavy chain variable domain which comprises an HCFR1 comprising the amino acid sequence as set forth as one of SEQ ID NOs: 33, 41 and 55; an HCFR2 comprising the amino acid sequence as set forth as one of SEQ ID NOs: 34, 42 and 51; an HCFR3 comprising the amino acid sequence as set forth as one of SEQ ID NOs: 35, 43, 48, 52 and 56; and an HCFR4 comprising the amino acid sequence as set forth as one of SEQ ID NOs: 37 and 45, wherein the sequence of each framework region may differ from the given sequence at up to five amino acid positions.

4. The CAR of claim 1, wherein:
(a) the light chain variable domain comprises the amino acid sequence as set forth as one of SEQ ID NOs: 3, 4, 5, 6, 7 and 8, or a sequence having at least 90% identity thereto; or
(b) the light chain variable domain comprises the amino acid sequence as set forth as one of SEQ ID NOs: 4, 5, 6, 7 and 8, or a sequence having at least 90% identity thereto.

5. The CAR of claim 1, wherein:
(a) the heavy chain variable domain comprises the amino acid sequence as set forth as one of SEQ ID NOs: 9, 10, 11, 12, 13 and 14, or a sequence having at least 90% identity thereto; or
(b) the heavy chain variable domain comprises the amino acid sequence as set forth as one of SEQ ID NOs: 10, 11, 12, 13 and 14, or a sequence having at least 90% identity thereto.

6. The CAR of claim 1, wherein:
(a) the light chain variable domain comprises the amino acid sequence as set forth as one of SEQ ID NOs: 4, 5, 6, 7 and 8, or a sequence having at least 90% identity thereto; and
the heavy chain variable domain comprises the amino acid sequence as set forth as one of SEQ ID NOs: 10, 11, 12, 13 and 14, or a sequence having at least 90% identity thereto; or
(b) the light chain variable domain comprises the amino acid sequence as set forth as SEQ ID NO: 4 or a sequence having at least 90% identity thereto; and
the heavy chain variable domain comprises the amino acid sequence as set forth as one of SEQ ID NOs: 10, 12 and 13 or a sequence having at least 90% identity thereto.

7. The CAR of claim 1, wherein:
(a) the light chain variable domain comprises the amino acid sequence as set forth as SEQ ID NO: 3 and the heavy chain variable domain comprises the amino acid sequence as set forth as SEQ ID NO: 9;
(b) the light chain variable domain comprises the amino acid sequence as set forth as SEQ ID NO: 4 and the heavy chain variable domain comprises the amino acid sequence as set forth as SEQ ID NO: 10;
(c) the light chain variable domain comprises the amino acid sequence as set forth as SEQ ID NO: 5 and the heavy chain variable domain comprises the amino acid sequence as set forth as SEQ ID NO: 11;
(d) the light chain variable domain comprises the amino acid sequence as set forth as SEQ ID NO: 6 and the heavy chain variable domain comprises the amino acid sequence as set forth as SEQ ID NO: 12;
(e) the light chain variable domain comprises the amino acid sequence as set forth as SEQ ID NO: 7 and the heavy chain variable domain comprises the amino acid sequence as set forth as SEQ ID NO: 13; or
(f) the light chain variable domain comprises the amino acid sequence as set forth as SEQ ID NO: 8 and the heavy chain variable domain comprises the amino acid sequence as set forth as SEQ ID NO: 14,
wherein each light chain variable domain and heavy chain variable domain above may have at least 90% identity to the amino acid sequence set forth above.

8. A chimeric antigen receptor (CAR) which comprises an antigen binding domain which selectively binds to Receptor Tyrosine Kinase Like Orphan Receptor 1 (ROR1), wherein the antigen binding domain comprises a light chain variable domain and a heavy chain variable domain, wherein:
(a) the light chain variable domain comprises the amino acid sequence as set forth as SEQ ID NO: 3 and the heavy chain variable domain comprises the amino acid sequence as set forth as SEQ ID NO: 9;
(b) the light chain variable domain comprises the amino acid sequence as set forth as SEQ ID NO: 4 and the heavy chain variable domain comprises the amino acid sequence as set forth as SEQ ID NO: 10;
(c) the light chain variable domain comprises the amino acid sequence as set forth as SEQ ID NO: 5 and the heavy chain variable domain comprises the amino acid sequence as set forth as SEQ ID NO: 11;
(d) the light chain variable domain comprises the amino acid sequence as set forth as SEQ ID NO: 6 and the heavy chain variable domain comprises the amino acid sequence as set forth as SEQ ID NO: 12;
(e) the light chain variable domain comprises the amino acid sequence as set forth as SEQ ID NO: 7 and the heavy chain variable domain comprises the amino acid sequence as set forth as SEQ ID NO: 13; or
(f) the light chain variable domain comprises the amino acid sequence as set forth as SEQ ID NO: 8 and the heavy chain variable domain comprises the amino acid sequence as set forth as SEQ ID NO: 14.

9. The CAR of claim 1 or 8 which comprises an endodomain, wherein the endodomain comprises:
(a) a CD3-Zeta T cell signalling domain;
(b) CD28, OX40 and CD3-Zeta endodomains; or
(c) 41BB and CD3-Zeta endodomains.

10. An isolated nucleic acid encoding the CAR of claim 1 or 8.

11. An isolated host cell which comprises a CAR according to claim 1 or 8.

12. The host cell of claim 11, wherein the host cell is a T cell.

13. An isolated nucleic acid encoding:
a light chain variable domain comprising a light chain complementarity determining region (LCDR)1, an LCDR2 and an LCDR3, wherein LCDR1 comprises the amino acid sequence set forth in SEQ ID NO: 16; LCDR2 comprises the amino acid sequence set forth in SEQ ID NO: 18; and LCDR3 comprises the amino acid sequence set forth in SEQ ID NO: 20;
or a heavy chain variable domain comprising a heavy chain complementarity determining region (HCDR)1, an HCDR2 and an HCDR3, wherein HCDR1 comprises the amino acid sequence set forth in SEQ ID NO: 23; HCDR2 comprises the amino acid sequence set forth in SEQ ID NO: 25; and HCDR3 comprises the amino acid sequence set forth in SEQ ID NO: 57.

14. A method for making a cell engineered to express a CAR which comprises the step of transducing or transfecting a cell with a nucleic acid sequence according to claim 13.

15. A method for treating a ROR1-expressing cancer comprising administering to a subject the engineered cell according to claim 14 to cause selective depletion of malignant cells.

16. A method according to claim 15 wherein the ROR1-expressing cancer is leukaemia, pancreatic cancer, prostate cancer, colon cancer, bladder cancer, ovarian cancer, glioblastoma, testicular cancer, uterine cancer, adrenal cancer, breast cancer, lung cancer, melanoma, neuroblastoma, sarcoma or renal cancer.

* * * * *

SEQUENCE LISTING

<160> NUMBER OF SEQ ID NOS: 62

<210> SEQ ID NO 1
<211> LENGTH: 15
<212> TYPE: PRT
<213> ORGANISM: Artificial sequence
<220> FEATURE:
<223> OTHER INFORMATION: Linker

<400> SEQUENCE: 1

```
Gly Gly Gly Gly Ser Gly Gly Gly Ser Gly Gly Gly Ser
1               5                   10                  15
```

<210> SEQ ID NO 2
<211> LENGTH: 5
<212> TYPE: PRT
<213> ORGANISM: Artificial sequence
<220> FEATURE:
<223> OTHER INFORMATION: Linker

<400> SEQUENCE: 2

```
Gly Gly Gly Gly Ser
1               5
```

<210> SEQ ID NO 3
<211> LENGTH: 107
<212> TYPE: PRT
<213> ORGANISM: Rattus norvegicus

<400> SEQUENCE: 3

```
Asp Ile Gln Met Thr Gln Ser Pro Ser Phe Leu Ser Ala Ser Val Gly
1               5                   10                  15

Asp Arg Val Thr Ile Asn Cys Lys Ala Ser Gln Asn Ile Asp Arg Tyr
            20                  25                  30

Leu Asn Trp Tyr Gln Gln Lys Leu Gly Glu Ala Pro Lys Arg Leu Leu
        35                  40                  45

Tyr Asn Thr Asn Lys Leu Gln Thr Gly Ile Pro Ser Arg Phe Ser Gly
    50                  55                  60

Ser Gly Ser Ala Thr Asp Phe Thr Leu Thr Ile Ser Ser Leu Gln Pro
65                  70                  75                  80

Glu Asp Phe Ala Thr Tyr Phe Cys Leu Gln Tyr Asn Ser Leu Pro Leu
                85                  90                  95

Thr Phe Gly Ser Gly Thr Lys Leu Glu Ile Lys
            100                 105
```

<210> SEQ ID NO 4
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 4

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Arg Tyr
            20                  25                  30

Leu Asn Trp Tyr Gln Gln Lys Pro Gly Lys Ala Pro Lys Arg Leu Ile
        35                  40                  45

Tyr Asn Thr Asn Lys Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Leu Pro Leu
                85                  90                  95

Thr Phe Gly Gln Gly Thr Lys Leu Glu Ile Lys
            100                 105
```

<210> SEQ ID NO 5
<211> LENGTH: 107

```
<212> TYPE: PRT
<213> ORGANISM: Artificial sequence
<220> FEATURE:
<223> OTHER INFORMATION: Humanised light chain variable region

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Arg Tyr
            20                  25                  30

Leu Asn Trp Phe Gln Gln Lys Pro Gly Lys Ala Pro Lys Ser Leu Ile
        35                  40                  45

Tyr Asn Thr Asn Lys Leu Gln Thr Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asn Ser Leu Pro Leu
                85                  90                  95

Thr Phe Gly Gln Gly Thr Arg Leu Glu Ile Lys
            100                 105

<210> SEQ ID NO 6
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Arg Tyr
            20                  25                  30

Leu Asn Trp Tyr Gln Gln Lys Pro Gly Lys Ala Pro Lys Leu Leu Ile
        35                  40                  45

Tyr Asn Thr Asn Lys Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asn Ser Leu Pro Leu
                85                  90                  95

Thr Phe Gly Gln Gly Thr Lys Leu Glu Ile Lys
            100                 105

<210> SEQ ID NO 7
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 7

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Ile Asp Arg Tyr
            20                  25                  30

Leu Asn Trp Tyr Gln Gln Lys Pro Gly Lys Ala Pro Lys Leu Leu Ile
        35                  40                  45

Tyr Asn Thr Asn Lys Leu Gln Thr Gly Val Pro Ser Arg Phe Ser Gly
```

```
                    50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Asn Ser Leu Pro Leu
                     85                  90                  95

Thr Phe Gly Gln Gly Thr Lys Leu Glu Ile Lys
                100                 105

<210> SEQ ID NO 8
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 8

Asp Ile Gln Met Thr Gln Ser Pro Ser Thr Leu Ser Ala Ser Val Gly
  1               5                  10                  15

Asp Arg Val Thr Ile Thr Cys Lys Ala Ser Gln Asn Ile Asp Arg Tyr
                 20                  25                  30

Leu Asn Trp Tyr Gln Gln Lys Pro Gly Lys Ala Pro Lys Leu Leu Ile
             35                  40                  45

Tyr Asn Thr Asn Lys Leu Gln Thr Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Leu Gln Tyr Asn Ser Leu Pro Leu
                     85                  90                  95

Thr Phe Gly Gln Gly Thr Lys Leu Glu Ile Lys
                100                 105

<210> SEQ ID NO 9
<211> LENGTH: 117
<212> TYPE: PRT
<213> ORGANISM: Rattus norvegicus

<400> SEQUENCE: 9

Glu Val Gln Leu Val Glu Ser Gly Gly Gly Leu Val Gln Pro Gly Arg
  1               5                  10                  15

Ser Leu Lys Leu Ser Cys Ala Ala Ser Gly Phe Ile Phe Ser Glu His
                 20                  25                  30

Asn Met Ala Trp Val Arg Gln Ala Pro Lys Lys Gly Leu Glu Trp Val
             35                  40                  45

Ala Thr Ile Ser Asp Asp Gly Arg Asn Thr Tyr Tyr Arg Asp Ser Met
 50                  55                  60

Arg Gly Arg Phe Thr Ile Ser Arg Glu Asn Ala Arg Ser Thr Leu Tyr
 65                  70                  75                  80

Leu Gln Leu Asp Ser Leu Arg Ser Glu Asp Thr Ala Thr Tyr Tyr Cys
                 85                  90                  95

Ala Ser His Arg Tyr Asn Leu Phe Asp Ser Trp Gly Gln Gly Val Met
                100                 105                 110

Val Thr Val Ser Ser
        115

<210> SEQ ID NO 10
<211> LENGTH: 117
<212> TYPE: PRT
<213> ORGANISM: Artificial sequence
```

```
<220> FEATURE:
<223> OTHER INFORMATION: Humanised heavy chain variable region

<400> SEQUENCE: 10

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Glu His
            20                  25                  30

Asn Met Ala Trp Val Arg Gln Ala Pro Gly Lys Gly Leu Glu Trp Val
        35                  40                  45

Ala Thr Ile Ser Asp Asp Gly Arg Asn Thr Tyr Tyr Arg Asp Ser Met
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ser His Arg Tyr Asn Leu Phe Asp Ser Trp Gly Gln Gly Thr Met
            100                 105                 110

Val Thr Val Ser Ser
        115

<210> SEQ ID NO 11
<211> LENGTH: 117
<212> TYPE: PRT
<213> ORGANISM: Artificial sequence
<220> FEATURE:
<223> OTHER INFORMATION: Humanised heavy chain variable region

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Glu His
            20                  25                  30

Asn Met Ala Trp Val Arg Gln Ala Pro Gly Lys Gly Leu Glu Trp Val
        35                  40                  45

Ser Thr Ile Ser Asp Asp Gly Arg Asn Thr Tyr Tyr Arg Asp Ser Met
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Arg Tyr Asn Leu Phe Asp Ser Trp Gly Gln Gly Thr Leu
            100                 105                 110

Val Thr Val Ser Ser
        115

<210> SEQ ID NO 12
<211> LENGTH: 117
<212> TYPE: PRT
<213> ORGANISM: Artificial sequence
<220> FEATURE:
<223> OTHER INFORMATION: Humanised heavy chain variable region

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Glu His
            20                  25                  30
```

```
Asn Met Ala Trp Val Arg Gln Ala Pro Gly Lys Gly Leu Glu Trp Val
            35                  40                  45

Ala Thr Ile Ser Asp Asp Gly Arg Asn Thr Tyr Tyr Arg Asp Ser Met
 50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg His Arg Tyr Asn Leu Phe Asp Ser Trp Gly Gln Gly Thr Met
            100                 105                 110

Val Thr Val Ser Ser
            115

<210> SEQ ID NO 13
<211> LENGTH: 117
<212> TYPE: PRT
<213> ORGANISM: Artificial sequence
<220> FEATURE:
<223> OTHER INFORMATION: Humanised heavy chain variable region

<400> SEQUENCE: 13

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ile Phe Ser Glu His
            20                  25                  30

Asn Met Ala Trp Val Arg Gln Ala Pro Gly Lys Gly Leu Val Trp Val
            35                  40                  45

Ser Thr Ile Ser Asp Asp Gly Arg Asn Thr Tyr Tyr Arg Asp Ser Met
 50                  55                  60

Arg Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg His Arg Tyr Asn Leu Phe Asp Ser Trp Gly Gln Gly Thr Leu
            100                 105                 110

Val Thr Val Ser Ser
            115

<210> SEQ ID NO 14
<211> LENGTH: 117
<212> TYPE: PRT
<213> ORGANISM: Artificial sequence
<220> FEATURE:
<223> OTHER INFORMATION: Humanised heavy chain variable region

<400> SEQUENCE: 14

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Ile Phe Ser Glu His
            20                  25                  30

Asn Met Ala Trp Val Arg Gln Ala Pro Gly Lys Gly Leu Glu Trp Val
            35                  40                  45

Ser Thr Ile Ser Asp Asp Gly Arg Asn Thr Tyr Tyr Arg Asp Ser Met
 50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95
```

-continued

Ala Lys His Arg Tyr Asn Leu Phe Asp Ser Trp Gly Gln Gly Thr Leu
            100                 105                 110

Val Thr Val Ser Ser
        115

<210> SEQ ID NO 15
<211> LENGTH: 26
<212> TYPE: PRT
<213> ORGANISM: Rattus norvegicus

<400> SEQUENCE: 15

Asp Ile Gln Met Thr Gln Ser Pro Ser Phe Leu Ser Ala Ser Val Gly
1               5                   10                  15

Asp Arg Val Thr Ile Asn Cys Lys Ala Ser
            20                  25

<210> SEQ ID NO 16
<211> LENGTH: 6
<212> TYPE: PRT
<213> ORGANISM: Rattus norvegicus

<400> SEQUENCE: 16

Gln Asn Ile Asp Arg Tyr
1               5

<210> SEQ ID NO 17
<211> LENGTH: 17
<212> TYPE: PRT
<213> ORGANISM: Rattus norvegicus

<400> SEQUENCE: 17

Leu Asn Trp Tyr Gln Gln Lys Leu Gly Glu Ala Pro Lys Arg Leu Leu
1               5                   10                  15

Tyr

<210> SEQ ID NO 18
<211> LENGTH: 3
<212> TYPE: PRT
<213> ORGANISM: Rattus norvegicus

<400> SEQUENCE: 18

Asn Thr Asn
1

<210> SEQ ID NO 19
<211> LENGTH: 36
<212> TYPE: PRT
<213> ORGANISM: Rattus norvegicus

<400> SEQUENCE: 19

Lys Leu Gln Thr Gly Ile Pro Ser Arg Phe Ser Gly Ser Gly Ser Ala
1               5                   10                  15

Thr Asp Phe Thr Leu Thr Ile Ser Ser Leu Gln Pro Glu Asp Phe Ala
            20                  25                  30

Thr Tyr Phe Cys
        35

<210> SEQ ID NO 20
<211> LENGTH: 9
<212> TYPE: PRT
<213> ORGANISM: Rattus norvegicus

```
<400> SEQUENCE: 20

Leu Gln Tyr Asn Ser Leu Pro Leu Thr
1               5

<210> SEQ ID NO 21
<211> LENGTH: 10
<212> TYPE: PRT
<213> ORGANISM: Rattus norvegicus

<400> SEQUENCE: 21

Phe Gly Ser Gly Thr Lys Leu Glu Ile Lys
1               5                   10

<210> SEQ ID NO 22
<211> LENGTH: 25
<212> TYPE: PRT
<213> ORGANISM: Rattus norvegicus

<400> SEQUENCE: 22

Glu Val Gln Leu Val Glu Ser Gly Gly Gly Leu Val Gln Pro Gly Arg
1               5                   10                  15

Ser Leu Lys Leu Ser Cys Ala Ala Ser
            20                  25

<210> SEQ ID NO 23
<211> LENGTH: 8
<212> TYPE: PRT
<213> ORGANISM: Rattus norvegicus

<400> SEQUENCE: 23

Gly Phe Ile Phe Ser Glu His Asn
1               5

<210> SEQ ID NO 24
<211> LENGTH: 17
<212> TYPE: PRT
<213> ORGANISM: Rattus norvegicus

<400> SEQUENCE: 24

Met Ala Trp Val Arg Gln Ala Pro Lys Lys Gly Leu Glu Trp Val Ala
1               5                   10                  15

Thr

<210> SEQ ID NO 25
<211> LENGTH: 8
<212> TYPE: PRT
<213> ORGANISM: Rattus norvegicus

<400> SEQUENCE: 25

Ile Ser Asp Asp Gly Arg Asn Thr
1               5

<210> SEQ ID NO 26
<211> LENGTH: 38
<212> TYPE: PRT
<213> ORGANISM: Rattus norvegicus

<400> SEQUENCE: 26

Tyr Tyr Arg Asp Ser Met Arg Gly Arg Phe Thr Ile Ser Arg Glu Asn
1               5                   10                  15

Ala Arg Ser Thr Leu Tyr Leu Gln Leu Asp Ser Leu Arg Ser Glu Asp
            20                  25                  30
```

Thr Ala Thr Tyr Tyr Cys
        35

<210> SEQ ID NO 27
<211> LENGTH: 10
<212> TYPE: PRT
<213> ORGANISM: Rattus norvegicus

<400> SEQUENCE: 27

Ala Ser His Arg Tyr Asn Leu Phe Asp Ser
1               5                   10

<210> SEQ ID NO 28
<211> LENGTH: 11
<212> TYPE: PRT
<213> ORGANISM: Rattus norvegicus

<400> SEQUENCE: 28

Trp Gly Gln Gly Val Met Val Thr Val Ser Ser
1               5                   10

<210> SEQ ID NO 29
<211> LENGTH: 26
<212> TYPE: PRT
<213> ORGANISM: Homo sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Lys Ala Ser
            20                  25

<210> SEQ ID NO 30
<211> LENGTH: 17
<212> TYPE: PRT
<213> ORGANISM: Homo sapiens

<400> SEQUENCE: 30

Leu Asn Trp Tyr Gln Gln Lys Pro Gly Lys Ala Pro Lys Arg Leu Ile
1               5                   10                  15

Tyr

<210> SEQ ID NO 31
<211> LENGTH: 36
<212> TYPE: PRT
<213> ORGANISM: Homo sapiens

<400> SEQUENCE: 31

Lys Leu Gln Thr Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Thr Tyr Tyr Cys
        35

<210> SEQ ID NO 32
<211> LENGTH: 10
<212> TYPE: PRT
<213> ORGANISM: Homo sapiens

<400> SEQUENCE: 32

Phe Gly Gln Gly Thr Lys Leu Glu Ile Lys
1               5                   10

<210> SEQ ID NO 33
<211> LENGTH: 25
<212> TYPE: PRT
<213> ORGANISM: Homo sapiens

<400> SEQUENCE: 33

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 34
<211> LENGTH: 17
<212> TYPE: PRT
<213> ORGANISM: Homo sapiens

<400> SEQUENCE: 34

Met Ala Trp Val Arg Gln Ala Pro Gly Lys Gly Leu Glu Trp Val Ala
1               5                   10                  15

Thr

<210> SEQ ID NO 35
<211> LENGTH: 40
<212> TYPE: PRT
<213> ORGANISM: Homo sapiens

<400> SEQUENCE: 35

Tyr Tyr Arg Asp Ser Met Arg Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys Thr Ser
        35                  40

<210> SEQ ID NO 36
<211> LENGTH: 10
<212> TYPE: PRT
<213> ORGANISM: Artificial sequence
<220> FEATURE:
<223> OTHER INFORMATION: Humanised heavy chain CDR3

<400> SEQUENCE: 36

Thr Ser His Arg Tyr Asn Leu Phe Asp Ser
1               5                   10

<210> SEQ ID NO 37
<211> LENGTH: 11
<212> TYPE: PRT
<213> ORGANISM: Homo sapiens

<400> SEQUENCE: 37

Trp Gly Gln Gly Thr Met Val Thr Val Ser Ser
1               5                   10

<210> SEQ ID NO 38
<211> LENGTH: 17
<212> TYPE: PRT
<213> ORGANISM: Homo sapiens

<400> SEQUENCE: 38

Leu Asn Trp Phe Gln Gln Lys Pro Gly Lys Ala Pro Lys Ser Leu Ile
1               5                   10                  15

Tyr

<210> SEQ ID NO 39
<211> LENGTH: 36
<212> TYPE: PRT
<213> ORGANISM: Homo sapiens

<400> SEQUENCE: 39

```
Lys Leu Gln Thr Gly Val Pro Ser Lys Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35
```

<210> SEQ ID NO 40
<211> LENGTH: 10
<212> TYPE: PRT
<213> ORGANISM: Homo sapiens

<400> SEQUENCE: 40

```
Phe Gly Gln Gly Thr Arg Leu Glu Ile Lys
1               5                   10
```

<210> SEQ ID NO 41
<211> LENGTH: 25
<212> TYPE: PRT
<213> ORGANISM: Homo sapiens

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 42
<211> LENGTH: 17
<212> TYPE: PRT
<213> ORGANISM: Homo sapiens

<400> SEQUENCE: 42

```
Met Ala Trp Val Arg Gln Ala Pro Gly Lys Gly Leu Glu Trp Val Ser
1               5                   10                  15

Thr
```

<210> SEQ ID NO 43
<211> LENGTH: 40
<212> TYPE: PRT
<213> ORGANISM: Homo sapiens

<400> SEQUENCE: 43

```
Tyr Tyr Arg Asp Ser Met Arg Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys Ala Lys
        35                  40
```

<210> SEQ ID NO 44
<211> LENGTH: 10
<212> TYPE: PRT

<213> ORGANISM: Artificial sequence
<220> FEATURE:
<223> OTHER INFORMATION: Humanised heavy chain CDR3

<400> SEQUENCE: 44

Ala Lys His Arg Tyr Asn Leu Phe Asp Ser
1               5                   10

<210> SEQ ID NO 45
<211> LENGTH: 11
<212> TYPE: PRT
<213> ORGANISM: Homo sapiens

<400> SEQUENCE: 45

Trp Gly Gln Gly Thr Leu Val Thr Val Ser Ser
1               5                   10

<210> SEQ ID NO 46
<211> LENGTH: 17
<212> TYPE: PRT
<213> ORGANISM: Homo sapiens

<400> SEQUENCE: 46

Leu Asn Trp Tyr Gln Gln Lys Pro Gly Lys Ala Pro Lys Leu Leu Ile
1               5                   10                  15

Tyr

<210> SEQ ID NO 47
<211> LENGTH: 36
<212> TYPE: PRT
<213> ORGANISM: Homo sapiens

<400> SEQUENCE: 47

Lys Leu Gln Thr Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 48
<211> LENGTH: 40
<212> TYPE: PRT
<213> ORGANISM: Homo sapiens

<400> SEQUENCE: 48

Tyr Tyr Arg Asp Ser Met Arg Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys Ala Arg
        35                  40

<210> SEQ ID NO 49
<211> LENGTH: 10
<212> TYPE: PRT
<213> ORGANISM: Artificial sequence
<220> FEATURE:
<223> OTHER INFORMATION: Humanised heavy chain CDR3

<400> SEQUENCE: 49

Ala Arg His Arg Tyr Asn Leu Phe Asp Ser
1               5                   10

<210> SEQ ID NO 50
<211> LENGTH: 26
<212> TYPE: PRT
<213> ORGANISM: Homo sapiens

<400> SEQUENCE: 50

Asp Ile Gln Leu Thr Gln Ser Pro Ser Phe Leu Ser Ala Ser Val Gly
1               5                   10                  15

Asp Arg Val Thr Ile Thr Cys Lys Ala Ser
            20                  25

<210> SEQ ID NO 51
<211> LENGTH: 17
<212> TYPE: PRT
<213> ORGANISM: Homo sapiens

<400> SEQUENCE: 51

Met Ala Trp Val Arg Gln Ala Pro Gly Lys Gly Leu Val Trp Val Ser
1               5                   10                  15

Thr

<210> SEQ ID NO 52
<211> LENGTH: 40
<212> TYPE: PRT
<213> ORGANISM: Homo sapiens

<400> SEQUENCE: 52

Tyr Tyr Arg Asp Ser Met Arg Gly Arg Phe Thr Ile Ser Arg Asp Asn
1               5                   10                  15

Ala Lys Asn Thr Leu Tyr Leu Gln Met Asn Ser Leu Arg Ala Glu Asp
            20                  25                  30

Thr Ala Val Tyr Tyr Cys Ala Arg
        35                  40

<210> SEQ ID NO 53
<211> LENGTH: 26
<212> TYPE: PRT
<213> ORGANISM: Homo sapiens

<400> SEQUENCE: 53

Asp Ile Gln Met Thr Gln Ser Pro Ser Thr Leu Ser Ala Ser Val Gly
1               5                   10                  15

Asp Arg Val Thr Ile Thr Cys Lys Ala Ser
            20                  25

<210> SEQ ID NO 54
<211> LENGTH: 36
<212> TYPE: PRT
<213> ORGANISM: Homo sapiens

<400> SEQUENCE: 54

Lys Leu Gln Thr Gly Val Pro Ser Arg Phe Ser Gly Ser Gly Ser Gly
1               5                   10                  15

Thr Glu Phe Thr Leu Thr Ile Ser Ser Leu Gln Pro Asp Asp Phe Ala
            20                  25                  30

Thr Tyr Tyr Cys
        35

<210> SEQ ID NO 55
<211> LENGTH: 25

```
<212> TYPE: PRT
<213> ORGANISM: Homo sapiens

<400> SEQUENCE: 55

Glu Val Gln Leu Val Glu Ser Gly Gly Gly Leu Val Gln Pro Gly Arg
1               5                   10                  15

Ser Leu Arg Leu Ser Cys Ala Ala Ser
            20                  25

<210> SEQ ID NO 56
<211> LENGTH: 40
<212> TYPE: PRT
<213> ORGANISM: Homo sapiens

<400> SEQUENCE: 56

Tyr Tyr Arg Asp Ser Met Arg Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Leu Tyr Tyr Cys Ala Lys
        35                  40

<210> SEQ ID NO 57
<211> LENGTH: 10
<212> TYPE: PRT
<213> ORGANISM: Artificial sequence
<220> FEATURE:
<223> OTHER INFORMATION: Heavy chain CDR3
<220> FEATURE:
<221> NAME/KEY: misc_feature
<222> LOCATION: (1)..(1)
<223> OTHER INFORMATION: Xaa can be Ala or Thr
<220> FEATURE:
<221> NAME/KEY: misc_feature
<222> LOCATION: (2)..(2)
<223> OTHER INFORMATION: Xaa can be Ser, Lys or Arg

<400> SEQUENCE: 57

Xaa Xaa His Arg Tyr Asn Leu Phe Asp Ser
1               5                   10

<210> SEQ ID NO 58
<211> LENGTH: 11
<212> TYPE: PRT
<213> ORGANISM: Rattus norvegicus

<400> SEQUENCE: 58

Lys Ala Ser Gln Asn Ile Asp Arg Tyr Leu Asn
1               5                   10

<210> SEQ ID NO 59
<211> LENGTH: 7
<212> TYPE: PRT
<213> ORGANISM: Rattus norvegicus

<400> SEQUENCE: 59

Asn Thr Asn Lys Leu Gln Thr
1               5

<210> SEQ ID NO 60
<211> LENGTH: 5
<212> TYPE: PRT
<213> ORGANISM: Rattus norvegicus

<400> SEQUENCE: 60
```

```
Glu His Asn Met Ala
1               5

<210> SEQ ID NO 61
<211> LENGTH: 17
<212> TYPE: PRT
<213> ORGANISM: Rattus norvegicus

<400> SEQUENCE: 61

Thr Ile Ser Asp Asp Gly Arg Asn Thr Tyr Tyr Arg Asp Ser Met Arg
1               5                   10                  15

Gly

<210> SEQ ID NO 62
<211> LENGTH: 8
<212> TYPE: PRT
<213> ORGANISM: Rattus norvegicus

<400> SEQUENCE: 62

His Arg Tyr Asn Leu Phe Asp Ser
1               5
```